(12) United States Patent
McFarlin et al.

(10) Patent No.: US 11,980,465 B2
(45) Date of Patent: May 14, 2024

(54) SYSTEM AND METHOD FOR OMNI-DIRECTIONAL BIPOLAR STIMULATION OF NERVE TISSUE OF A PATIENT VIA A BIPOLAR STIMULATION PROBE

(71) Applicant: Medtronic Xomed, Inc., Jacksonville, FL (US)

(72) Inventors: Kevin L. McFarlin, St. Johns, FL (US); Bryan L. Courtney, Jacksonville, FL (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 728 days.

(21) Appl. No.: 14/678,452

(22) Filed: Apr. 3, 2015

(65) Prior Publication Data

US 2016/0287112 A1    Oct. 6, 2016

(51) Int. Cl.
| | |
|---|---|
| *A61B 5/00* | (2006.01) |
| *A61B 5/24* | (2021.01) |
| *A61N 1/04* | (2006.01) |

(52) U.S. Cl.
CPC ............. *A61B 5/24* (2021.01); *A61B 5/0048* (2013.01); *A61B 5/4041* (2013.01); *A61N 1/0456* (2013.01)

(58) Field of Classification Search
CPC .... A61B 5/04001; A61B 5/4041–4052; A61B 2018/00654; A61B 2018/00708;
(Continued)

(56) References Cited

U.S. PATENT DOCUMENTS

| | | | |
|---|---|---|---|
| 4,265,237 A | 5/1981 | Schwanbom et al. | |
| 4,630,263 A | 12/1986 | Townsend et al. | |

(Continued)

FOREIGN PATENT DOCUMENTS

| | | |
|---|---|---|
| AU | 2016244152 A1 | 11/2017 |
| CA | 2957385 A1 | 2/2016 |

(Continued)

OTHER PUBLICATIONS

International Preliminary Report on Patentability dated Oct. 12, 2017 in corresponding/related International Application No. PCT/US2016/023910.

(Continued)

*Primary Examiner* — Kaylee R Wilson
*Assistant Examiner* — H. Q. Nguyen
(74) *Attorney, Agent, or Firm* — Carter, DeLuca & Farrell LLP

(57) ABSTRACT

A bipolar stimulation probe including a first electrode, a second electrode, a control module, and switches. The control module is configured to stimulate nerve tissue of a patient by generating (i) a first output signal indicative of a first pulse to be output from the first electrode, and (ii) a second output signal indicative of a second pulse to be output from the second electrode. The first pulse and the second pulse are monophasic. The switches are configured to output from the bipolar stimulation probe (i) the first pulse on the first electrode based on the first output signal, and (ii) the second pulse on the second electrode based on the second output signal.

17 Claims, 16 Drawing Sheets

(58) Field of Classification Search
CPC .. A61B 2018/00916; A61B 2018/0094; A61B
2018/00958; A61B 2018/124; A61B
2018/1246; A61B 2018/1253–126; A61N
1/0456
See application file for complete search history.

(56) References Cited

U.S. PATENT DOCUMENTS

| | | | |
|---|---|---|---|
| 5,116,332 A | 5/1992 | Lottick | |
| 5,767,791 A | 6/1998 | Stoop et al. | |
| 5,921,939 A | 7/1999 | Danielsson et al. | |
| 6,752,816 B2 | 6/2004 | Culp et al. | |
| 7,216,001 B2* | 5/2007 | Hacker | A61B 5/04001 607/63 |
| 7,236,822 B2 | 6/2007 | Dobak, III | |
| 7,292,886 B1* | 11/2007 | Kroll | A61N 1/368 607/122 |
| 7,496,407 B2 | 2/2009 | Odderson | |
| 7,689,292 B2 | 3/2010 | Hadzic et al. | |
| 7,789,833 B2 | 9/2010 | Urbano et al. | |
| 7,987,001 B2 | 7/2011 | Teichman et al. | |
| 7,993,269 B2 | 8/2011 | Donofrio et al. | |
| 8,068,910 B2 | 11/2011 | Gerber et al. | |
| 8,126,736 B2 | 2/2012 | Anderson et al. | |
| 8,255,045 B2 | 8/2012 | Gharib et al. | |
| 8,374,673 B2 | 2/2013 | Adcox et al. | |
| 8,498,717 B2 | 7/2013 | Lee et al. | |
| 8,515,520 B2 | 8/2013 | Brunnett et al. | |
| 8,568,312 B2 | 10/2013 | Cusimano Reaston et al. | |
| 8,568,317 B1 | 10/2013 | Gharib et al. | |
| 8,594,779 B2 | 11/2013 | Denison et al. | |
| 8,670,830 B2 | 3/2014 | Carlson et al. | |
| 8,680,986 B2 | 3/2014 | Costantino | |
| 8,688,237 B2 | 4/2014 | Stanislaus et al. | |
| 8,805,527 B2 | 8/2014 | Mumford et al. | |
| 8,886,280 B2 | 11/2014 | Kartush | |
| 8,892,259 B2 | 11/2014 | Bartol et al. | |
| 8,926,509 B2 | 1/2015 | Magar et al. | |
| 8,956,418 B2 | 2/2015 | Wasielewski et al. | |
| 8,989,855 B2 | 3/2015 | Murphy et al. | |
| 9,031,658 B2 | 5/2015 | Chiao et al. | |
| 9,078,671 B2 | 7/2015 | Beale et al. | |
| 9,084,550 B1 | 7/2015 | Bartol et al. | |
| 9,084,551 B2 | 7/2015 | Brunnett et al. | |
| 9,204,830 B2 | 12/2015 | Zand et al. | |
| 9,918,669 B2 | 3/2018 | Brown et al. | |
| 10,039,915 B2 | 8/2018 | McFarlin et al. | |
| 10,123,731 B2 | 11/2018 | Brown et al. | |
| 10,368,793 B2 | 8/2019 | Brown et al. | |
| 10,398,369 B2 | 9/2019 | Brown et al. | |
| 10,849,517 B2 | 12/2020 | Cantwell et al. | |
| 10,987,506 B2 | 4/2021 | McFarlin et al. | |
| 2002/0109621 A1 | 8/2002 | Khair et al. | |
| 2002/0111624 A1 | 8/2002 | Witt et al. | |
| 2003/0171747 A1 | 9/2003 | Kanehira et al. | |
| 2003/0181798 A1 | 9/2003 | Al-Ali | |
| 2004/0135528 A1 | 7/2004 | Yasohara et al. | |
| 2005/0075067 A1 | 4/2005 | Lawson et al. | |
| 2005/0075578 A1 | 4/2005 | Gharib et al. | |
| 2005/0085743 A1* | 4/2005 | Hacker | A61B 5/389 600/554 |
| 2005/0131464 A1* | 6/2005 | Heinrich | A61N 1/39622 607/4 |
| 2005/0149143 A1 | 7/2005 | Libbus et al. | |
| 2005/0159659 A1 | 7/2005 | Sawan et al. | |
| 2005/0215993 A1 | 9/2005 | Phan | |
| 2005/0267529 A1 | 12/2005 | Crockett et al. | |
| 2006/0025702 A1 | 2/2006 | Sterrantino et al. | |
| 2006/0200219 A1* | 9/2006 | Thrope | A61B 5/05 607/9 |
| 2006/0241725 A1 | 10/2006 | Libbus et al. | |
| 2006/0276702 A1 | 12/2006 | McGinnis | |
| 2007/0083193 A1 | 4/2007 | Werneth et al. | |
| 2007/0191915 A1 | 8/2007 | Strother et al. | |
| 2007/0260293 A1 | 11/2007 | Carpenter et al. | |
| 2007/0270678 A1 | 11/2007 | Fadem et al. | |
| 2007/0270918 A1 | 11/2007 | De Bel et al. | |
| 2007/0282217 A1 | 12/2007 | McGinnis et al. | |
| 2008/0051673 A1* | 2/2008 | Kong | A61B 5/05 600/546 |
| 2008/0077198 A1 | 3/2008 | Webb et al. | |
| 2008/0183190 A1* | 7/2008 | Adcox | A61B 34/20 606/130 |
| 2008/0183915 A1 | 7/2008 | Iima | |
| 2008/0214903 A1 | 9/2008 | Orbach | |
| 2008/0218393 A1 | 9/2008 | Kuramochi et al. | |
| 2008/0300650 A1 | 12/2008 | Gerber et al. | |
| 2008/0306348 A1 | 12/2008 | Kuo et al. | |
| 2009/0024187 A1 | 1/2009 | Erickson et al. | |
| 2009/0054804 A1 | 2/2009 | Gharib et al. | |
| 2009/0157141 A1 | 6/2009 | Chiao et al. | |
| 2009/0177112 A1 | 7/2009 | Gharib et al. | |
| 2009/0182322 A1 | 7/2009 | D'Amelio et al. | |
| 2009/0182328 A1 | 7/2009 | D'Amelio et al. | |
| 2009/0182330 A1 | 7/2009 | D'Amelio et al. | |
| 2009/0182331 A1 | 7/2009 | D'Amelio et al. | |
| 2009/0186577 A1 | 7/2009 | Ross et al. | |
| 2009/0240117 A1 | 9/2009 | Chmiel et al. | |
| 2009/0299439 A1 | 12/2009 | Mire et al. | |
| 2010/0036280 A1 | 2/2010 | Ballegaard et al. | |
| 2010/0130913 A1* | 5/2010 | Baynham | A61N 1/05 604/21 |
| 2010/0145178 A1 | 6/2010 | Kartush | |
| 2010/0152811 A1 | 6/2010 | Flaherty | |
| 2010/0152812 A1 | 6/2010 | Flaherty et al. | |
| 2010/0160731 A1 | 6/2010 | Giovannini et al. | |
| 2010/0168561 A1 | 7/2010 | Anderson | |
| 2010/0191311 A1 | 7/2010 | Scheiner et al. | |
| 2010/0280568 A1 | 11/2010 | Bulkes et al. | |
| 2011/0004207 A1* | 1/2011 | Wallace | A61N 1/0551 606/53 |
| 2011/0028860 A1 | 2/2011 | Chenaux et al. | |
| 2011/0071418 A1 | 3/2011 | Stellar et al. | |
| 2011/0160731 A1 | 6/2011 | Bleich et al. | |
| 2011/0190596 A1 | 8/2011 | Hacker et al. | |
| 2011/0230734 A1 | 9/2011 | Fain et al. | |
| 2011/0230782 A1 | 9/2011 | Bartol et al. | |
| 2011/0230783 A1 | 9/2011 | Bartol et al. | |
| 2011/0237924 A1 | 9/2011 | McGusty et al. | |
| 2011/0245647 A1 | 10/2011 | Stanislaus et al. | |
| 2011/0270120 A1 | 11/2011 | McFarlin et al. | |
| 2011/0270121 A1 | 11/2011 | Johnson et al. | |
| 2012/0004516 A1 | 1/2012 | Eng et al. | |
| 2012/0071784 A1 | 3/2012 | Melkent et al. | |
| 2012/0245439 A1 | 9/2012 | Andre et al. | |
| 2012/0330384 A1 | 12/2012 | Perryman et al. | |
| 2013/0030257 A1 | 1/2013 | Nakata et al. | |
| 2013/0090641 A1 | 4/2013 | McKinney et al. | |
| 2013/0116678 A1 | 5/2013 | Koss et al. | |
| 2013/0245722 A1 | 9/2013 | Ternes et al. | |
| 2013/0253334 A1 | 9/2013 | Al-Ali et al. | |
| 2013/0261422 A1 | 10/2013 | Gilmore et al. | |
| 2013/0304059 A1 | 11/2013 | Allen, IV et al. | |
| 2013/0345701 A1 | 12/2013 | Allen, IV et al. | |
| 2014/0005753 A1 | 1/2014 | Carbunaru | |
| 2014/0039491 A1* | 2/2014 | Bakos | A61B 18/1492 606/41 |
| 2014/0058284 A1 | 2/2014 | Bartol et al. | |
| 2014/0067007 A1 | 3/2014 | Drees et al. | |
| 2014/0073985 A1 | 3/2014 | Sakai et al. | |
| 2014/0074084 A1 | 3/2014 | Engeberg et al. | |
| 2014/0275849 A1 | 9/2014 | Acquista | |
| 2014/0275914 A1 | 9/2014 | Li et al. | |
| 2014/0277259 A1* | 9/2014 | Rosenberg | A61N 1/36071 607/46 |
| 2014/0303452 A1 | 10/2014 | Ghaffari | |
| 2014/0316229 A1* | 10/2014 | Tognetti | A61B 5/0205 600/383 |
| 2014/0336635 A1 | 11/2014 | Hart et al. | |
| 2014/0364920 A1 | 12/2014 | Doan et al. | |
| 2015/0012066 A1 | 1/2015 | Underwood | |
| 2015/0088029 A1 | 3/2015 | Wybo | |
| 2015/0112325 A1 | 4/2015 | Whitman | |

(56) References Cited

U.S. PATENT DOCUMENTS

| | | | |
|---|---|---|---|
| 2015/0157237 A1 | 6/2015 | Murphy et al. | |
| 2015/0173636 A1* | 6/2015 | Mokelke | A61B 18/1206 606/34 |
| 2015/0202395 A1 | 7/2015 | Fromentin | |
| 2015/0230749 A1 | 8/2015 | Gharib et al. | |
| 2015/0238260 A1 | 8/2015 | Nau, Jr. | |
| 2015/0250423 A1 | 9/2015 | Hacker et al. | |
| 2016/0015299 A1 | 1/2016 | Chan et al. | |
| 2016/0038072 A1 | 2/2016 | Brown et al. | |
| 2016/0038073 A1 | 2/2016 | Brown et al. | |
| 2016/0038074 A1 | 2/2016 | Brown et al. | |
| 2016/0038225 A1 | 2/2016 | Couture et al. | |
| 2016/0199659 A1 | 7/2016 | Jiang et al. | |
| 2016/0206362 A1 | 7/2016 | Mehta et al. | |
| 2016/0235999 A1 | 8/2016 | Nuta et al. | |
| 2016/0262699 A1 | 9/2016 | Goldstone et al. | |
| 2016/0270679 A1 | 9/2016 | Mahon et al. | |
| 2016/0287112 A1 | 10/2016 | McFarlin et al. | |
| 2016/0287861 A1 | 10/2016 | McFarlin et al. | |
| 2016/0317053 A1 | 11/2016 | Srivastava | |
| 2017/0202570 A1 | 7/2017 | Shelton, IV et al. | |
| 2017/0202598 A1 | 7/2017 | Shelton, IV et al. | |
| 2018/0078161 A1 | 3/2018 | Cantwell et al. | |
| 2019/0021643 A1 | 1/2019 | Brown et al. | |
| 2019/0021644 A1 | 1/2019 | Brown et al. | |

FOREIGN PATENT DOCUMENTS

| | | |
|---|---|---|
| CN | 2610843 Y | 4/2004 |
| CN | 101528303 A | 9/2009 |
| CN | 101594830 A | 12/2009 |
| CN | 101594906 A | 12/2009 |
| CN | 102046098 A | 5/2011 |
| CN | 102238904 A | 11/2011 |
| CN | 102762251 A | 10/2012 |
| CN | 103608069 A | 2/2014 |
| CN | 104203129 A | 12/2014 |
| CN | 105744887 A | 7/2016 |
| EP | 1587418 A1 | 10/2005 |
| GB | 2452158 A | 2/2009 |
| JP | 2004/500217 A | 1/2004 |
| JP | 2004/503266 A | 2/2004 |
| JP | 2008508049 A | 3/2008 |
| JP | 2008/519609 A | 6/2008 |
| JP | 2008538996 A | 11/2008 |
| JP | 2009/268016 A | 11/2009 |
| JP | 2010515487 A | 5/2010 |
| JP | 2011224085 A | 11/2011 |
| JP | 2012/516205 A | 7/2012 |
| JP | 2013/503015 A | 1/2013 |
| JP | 2013/506507 A | 2/2013 |
| JP | 2013505080 A | 2/2013 |
| JP | 2013/525002 A | 6/2013 |
| JP | 2014/117328 A | 6/2014 |
| JP | 2014524279 A | 9/2014 |
| JP | 2015513988 A | 5/2015 |
| JP | 2018/514258 A | 6/2018 |
| KR | 1020130052534 | 5/2013 |
| TW | I331027 B | 10/2010 |
| WO | WO 95/25472 * | 9/1995 |
| WO | WO-99/37359 A1 | 7/1999 |
| WO | 01/78831 A2 | 10/2001 |
| WO | WO-02/082982 A1 | 10/2002 |
| WO | 03026482 A2 | 4/2003 |
| WO | WO-2004064632 A1 | 8/2004 |
| WO | WO-2006/026482 A2 | 3/2006 |
| WO | 2008/012398 A1 | 1/2008 |
| WO | 2010/090835 A1 | 8/2010 |
| WO | 2011035311 A1 | 3/2011 |
| WO | 2011041684 A2 | 4/2011 |
| WO | 2011136962 A1 | 11/2011 |
| WO | WO-2011/150502 A2 | 12/2011 |
| WO | 2012129574 A2 | 9/2012 |
| WO | WO-2013/019757 A2 | 2/2013 |
| WO | WO-2013/151770 A1 | 10/2013 |
| WO | 2015-069962 A1 | 5/2015 |
| WO | 2015123100 A1 | 8/2015 |
| WO | 2016/160477 A1 | 10/2016 |

OTHER PUBLICATIONS

International Preliminary Report on Patentability dated Oct. 12, 2017 in corresponding/related International Application No. PCT/US2016/023903.
Hurley "Physiotherapy for Sleep Disturbance in Chronic Low Pack Pain: a Feasibility Randomised Controlled Trial" BMC Musculoskeletal Disorders; 11 pages; 2010.
Invitation to Pay Additional Fees dated Jun. 10, 2016 for International Application No. PCT/US2016/023903 which corresponds to U.S. Appl. No. 14/678,485, filed Apr. 3, 2015.
Wustrack "Change in Physical Activity One Year after Lumbar Decompression with or without Fusion, is it Correlated to Self-Reported Outcome Scores?" Proceedings of NASS 20th Annual Meeting/The Spine Journal 5 (2005) IS-189S.
Wustrack "Physical Activity does not correlate with HRQL Scores in Patients with Degeneratie Lumbar Conditions" Proceedings of the NASS 20th Annual Meeting/The Spine Journal 5 (2005) IS-189S.
Cypress Perform. SPI-based CyFi™ Transceiver Data Sheet. Cypress Semiconductor Corporation. (Jun. 25, 2009) pp. 1-45.
Australian Examination Report dated Dec. 8, 2018 in corresponding/related Australian Application No. 2016244152.
International Search Report and Written Opinion for PCT/US2015/043844 dated Jan. 12, 2016.
Australian Office Action dated Feb. 8, 2018 in corresponding/related Australian Application No. 2015301110.
Korean Office Action dated Aug. 21, 2018 in corresponding/related Korean Application No. 10-2017-7006340.
Canadian Office Action dated Dec. 11, 2017 in corresponding/related Canadian Application No. 2,957,385.
International Search Report and Written Opinion dated Nov. 29, 2017 in corresponding International Application No. PCT/US2017/051825.
Canadian Office Action dated Jul. 27, 2018 in corresponding/related Canadian Application No. 2,981,635.
Japanese Office Action dated Mar. 22, 2018 in corresponding/related Australian Application No. 2017-506854.
International Search Report and Written Opinion for PCT/US2016/023910 dated Aug. 5, 2016 which claims benefit of U.S. Appl. No. 14/578,452, filed Apr. 3, 2015.
International Search Report and Written Opinion for PCT/US2016/023903 dated Sep. 19, 2016 which claims benefit of U.S. Appl. No. 14/678,485, filed Apr. 3, 2015.
Office Action dated Feb. 20, 2019 in corresponding/related Korean Application No. 10-2017-7032059.
Japanese Office Action dated Nov. 26, 2018 in corresponding/related Japanese Application No. 2017-506854.
Office Action dated Feb. 13, 2019 in corresponding/related European Application No. 15753542.8.
International Preliminary Report on Patentability dated Mar. 28, 2019 in corresponding/related International Application No. PCT/US2017/051825.
Medtronic Xomed Inc. "APS Electrode Stimulator" Brochure, 10 pages, 2010.
Office Action dated Apr. 22, 2019 in corresponding/related Chinese Application No. 201580053580.3.
Office Action dated Jun. 20, 2019 in corresponding/related Canadian Application No. 2,981,635.
Office Action regarding Australian Patent Application No. 2016243081, dated Dec. 21, 2019.
Office Action regarding Canadian Patent Application No. 2957385, dated Dec. 12, 2019.
Office Action regarding Chinese Patent Application No. 201580053580.3, dated Jan. 7, 2020 (with English Translation).
Office Action regarding European Patent Application No. 16712713.3, dated Dec. 6, 2019.

(56) References Cited

OTHER PUBLICATIONS

Examination Report dated Feb. 28, 2020 in corresponding/related Australian Application No. 2019201702.
Office Action dated Feb. 26, 2020 in corresponding/related Japanese Application No. 2019-050923.
Office Action dated Feb. 5, 2020 in corresponding/related Indian Application No. 201717004436.
Office Action regarding corresponding/related Japanese Patent Application No. 2017552026, dated Mar. 27, 2020.
Office Action dated Apr. 14, 2020 in corresponding/related Chinese Application No. 201680030207.0.
Office Action dated Aug. 26, 2020 in corresponding/related Korean Application No. 10-2020-7007858.
Office Action dated Sep. 16, 2020 in corresponding/related Chinese Application No. 201680030207.0.
Extended European Search Report dated Jul. 1, 2020 in corresponding/related European Application No. 20176316.6.
Office Action dated Aug. 18, 2020 in corresponding/related Brazilian Application No. BR112017002470-5.
Office Action dated Aug. 26, 2020 in corresponding/related Korean Application No. 10-2019-7012435.
Office Action dated Jun. 30, 2020 in corresponding/related Chinese Application No. 201580053580.3.
Office Action dated Apr. 2, 2020 in corresponding/related Chinese Application No. 201680030281.2.
Examination Report dated Sep. 8, 2020, in corresponding/related Australian Application No. 2019203347.
Examination Report dated Sep. 8, 2020, in corresponding/related Australian Application No. 2019203348.
Office Action dated Nov. 3, 2020, in corresponding/related Canadian Application No. 2,957,385.
Office Action dated Nov. 10, 2020 in corresponding/related Japanese Application No. Japanese Patent Appln. No. 2017-552026.
Pre-Appeal Examination Report regarding Japanese Patent Application No. 2017-552026, dated Feb. 16, 2021.
Office Action regarding Chinese Patent Application No. 201580053580.3, dated Mar. 1, 2021.
Korean Office Action regarding Application No. 1020197010841, dated Feb. 3, 2022.
Office Action regarding Japanese Patent Application No. 2017-552026, dated Oct. 13, 2021 (with English Translation).
Rich Vogel, Understanding Anodal and Cathodal Stimulation, The ASNM Monitor, 2017, https://www.asnm.org/blogpost/1635804/290597/Understanding-Anodal-and-Cathodal-Stimulation.
Office Action regarding Japanese Patent Application No. 2020-134805, dated Jul. 13, 2021 with English translation.
Office Action regarding Japanese Patent Application No. 2020-135550, dated Jul. 5, 2021 with English translation.
Office Action regarding European Patent Application No. 16715204.0, dated May 21, 2021.
Japanese Office Action regarding Japanese Patent Application No. 2020-135550, dated Dec. 28, 2021.
Chinese Office Action regarding Application No. 201780071018.2, dated Aug. 24, 2021.
Canadian Examination Report regarding Application No. 2,981,636, dated Mar. 9, 2022.
Chinese Office Action regarding Patent Application No. 201780071018.2, dated Mar. 24, 2022.
Japanese Office Action regarding Patent Application No. 2019-515506, dated Apr. 22, 2022.
Japanese Office Action regarding Japanese Patent Application No. 2019515506, dated Feb. 4, 2022.
Canadian Office Action regarding Canadian Application No. 3099052, dated Feb. 18, 2022.
Japanese Office Action regarding Application No. 2020-134805, dated May 11, 2022.
European Office Action regarding Patent Application No. 20176316.6, dated Dec. 7, 2021.
First Office Action—Request for the submission of an Opinion, corresponding to Korean Patent Application No. 10-2017-7032060 (corresponding to PCT/US2016/023910), dated Oct. 26, 2022.
European Patent Office Brief Communication regarding Oral Proceedings, dated Jan. 12, 2023, corresponding to European Application No. 20176316.3.
Summons to Attend Oral Proceedings regarding European Patent Application No. 201763166, dated Sep. 26, 2022.
China-Decision on Rejection, corresponding to Chinese Application No. 201780071018.2, Date of Dispatch: Sep. 23, 2022.
European Patent Office—Office Action corresponding to EP 17 778 021.0, dated Nov. 22, 2022.

\* cited by examiner

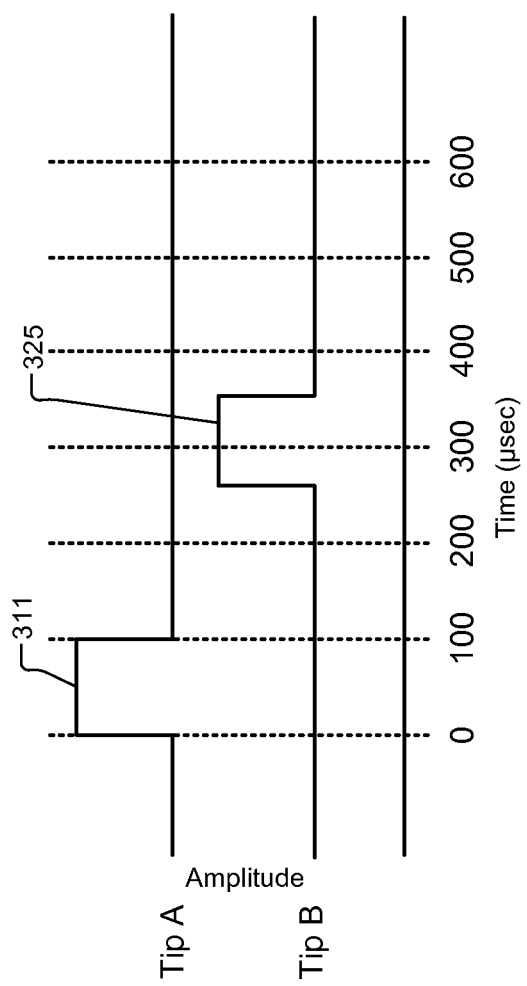

SYSTEM AND METHOD FOR OMNI-DIRECTIONAL BIPOLAR STIMULATION OF NERVE TISSUE OF A PATIENT VIA A BIPOLAR STIMULATION PROBE

CROSS-REFERENCE TO RELATED APPLICATIONS

The present disclosure is related to U.S. patent application Ser. No. 14/678,485 filed on Apr. 3, 2025, now U.S. Pat. No. 10,039,915, the entire contents of which are incorporated herein by reference.

FIELD

The present disclosure relates to nerve stimulation and nerve stimulators.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

A nerve of a patient may be stimulated by applying current to the nerve via a mono-polar stimulation probe. The mono-polar stimulation probe may include a stimulating electrode tip. A surgeon may touch a location on a patient with the electrode tip to provide a voltage and/or current to a location on the patient and stimulate nerve activity and as a result a muscle response (or muscle activity). A return (or anodal) needle may be attached: via a wire, to the mono-polar stimulation probe; and to the patient away from (i) sensors, and (ii) an area being stimulated. The sensors can include electrodes that are attached to the patient and used to monitor the muscle activity. Although the mono-polar stimulation probe is capable of providing deep focused penetration of applied current to a nerve, the mono-polar stimulation probe restricts movement of a hand of surgeon due to the attachment of the mono-polar stimulation probe to the return needle.

To eliminate use of the wire and return needle, a concentric probe, a side-by-side bipolar stimulation probe or a tri-polar stimulation probe may be used. The concentric probe includes an anodal (or central) electrode that extends within cathodal electrode. The anodal electrode is isolated from the cathodal electrode via an insulative shield around the anodal electrode. Although the concentric probe eliminates need of the wire and return needle associated with the mono-polar stimulation probe, current density and current tissue penetration is low.

The side-by-side bipolar stimulation probe and the tripolar stimulation probe are similar. The side-by-side bipolar stimulation probe includes two tips (an anodal electrode and a cathodal electrode). The tripolar stimulation probe has three tips (two cathodal electrodes and a single anodal electrode). The anodal electrode is positioned between the two cathodal electrodes. The tripolar stimulation probe is approximately 30% larger in size than the side-by-side bipolar stimulation probe due to the extra (or third) electrode.

The side-by-side bipolar stimulation probe has a single anodal electrode and a single cathodal electrode. Electrical current flowing through the two electrodes may be directly or indirectly applied to a nerve to stimulate the nerve. A negative electrical current may be applied to the nerve via the cathodal electrode (referred to as a cathode or negative electrode). The nerve resists excitation at the anodal electrode (referred to as an anode or positive electrode). This is a result of negative current from the cathode reducing voltage outside a neuronal cell membrane of the nerve, causing depolarization and an action potential. The anode injects positive current outside the neuronal cell membrane, which leads to hyperpolarization. Preferential cathodal stimulation refers to a reduced amount of current (one third to one quarter) needed to elicit a motor response of a muscle when the cathode is used as the stimulating electrode. The amount of current applied when the cathode is used is less than an amount of current needed to elicit a motor response of a muscle when the anode is used as the stimulating electrode. In order to stimulate a nerve using the cathode: the cathode may be attached to a stimulating needle or catheter; and the anode may be used as a current returning electrode and be attached to or in contact with the skin of the patient via a return wire.

When a surgeon uses a side-by-side bipolar stimulation probe, orientation of the electrodes of the side-by-side bipolar stimulation probe relative to a nerve influences an evoked response associated with the stimulation of the nerve. A nerve action potential evoked by the stimulation differs depending on the orientation of the electrodes relative to the nerve. The cathode of the bipolar stimulation probe must be placed distally along a nerve to evoke a proper response. In placing the cathode distally along the nerve, the cathode, relative to the anode, is directed away from an axonal head (or cell body) of a nerve and toward axon terminals of the nerve and/or a target muscle. If not oriented properly, no response or an improper response (e.g., an erratic signal or signal with low signal strength) may be generated.

Although electrodes of a side-by-side bipolar stimulation probe must be oriented properly relative to a nerve to obtain a proper response and to minimize an amount of current applied to receive a proper response, the electrodes may be improperly oriented for various reasons. For example, a surgeon may not be aware that the electrodes of the side-by-side bipolar stimulation probe needs to be oriented properly relative to a nerve. As another example, a surgeon may not be aware of an orientation of a nerve and as a result may not be aware of where an axonal head or a distal end of a nerve exists. For this reason, the surgeon may not be able to determine a proper orientation of electrodes of a side-by-side bipolar stimulation probe. As yet another example, a surgeon may not be aware of an orientation of electrodes of a bipolar stimulator on a nerve because of anatomical variation of nerves of a patient. Also, a surgeon may inadvertently change an orientation of electrodes of a side-by-side bipolar stimulation probe by simply rotating the side-by-side bipolar stimulation probe in a hand of the surgeon. These human factors may result in the side-by-side bipolar stimulation probe failing to evoke a proper response from a nerve. As a result, a surgeon may inadvertently resect nerve tissue that is thought not to be nerve tissue due to a negligible muscle response and/or lack of a detected muscle response.

SUMMARY

A bipolar stimulation probe is provided and includes a first electrode, a second electrode, a control module, and switches. The control module is configured to stimulate nerve tissue of a patient by generating (i) a first output signal indicative of a first pulse to be output from the first electrode, and (ii) a second output signal indicative of a second pulse to be output from the second electrode. The first pulse and the second pulse are monophasic. The switches are configured to output from the bipolar stimulation probe (i) the first pulse on the first electrode based on the first output signal, and (ii) the second pulse on the second electrode based on the second output signal.

In other features, a method of operating a bipolar stimulation probe is provided. The bipolar stimulation probe includes a first electrode and a second electrode. The method includes: generating a first output signal indicative of a first pulse to be output from the first electrode; and generating a second output signal indicative of a second pulse to be output from the second electrode. The first pulse and the second pulse are monophasic and are generated to stimulate nerve tissue of a patient. The method further includes, via a plurality of switches, outputting from the bipolar stimulation probe (i) the first pulse on the first electrode based on the first output signal, and (ii) the second pulse on the second electrode based on the second output signal.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

FIG. 8 is a bipolar signal plot of signals generated by a stimulation probe in accordance with the present disclosure.

In the drawings, reference numbers may be reused to identify similar and/or identical elements.

DESCRIPTION

To overcome the disadvantages associated with a monopolar stimulation probe, a concentric stimulation probe, a side-by-side bipolar stimulation probe and a tri-polar stimulation probe, bipolar stimulation probes and corresponding systems and methods are disclosed herein. The below disclosed bipolar stimulation probe examples: eliminate the need for a return needle and correspond wire; provide stimulated nerve penetration associated with a bipolar stimulation probe; and provide preferential cathodal stimulation with a stable muscle response. The disclosed examples eliminate the need to properly orient electrodes of a bipolar stimulation probe while preventing false negatives associated with traditional bipolar stimulation probe designs. The disclosed examples provide deeper tissue penetration than concentric probe designs while providing approximately 30% smaller probe tip designs than traditional tri-polar probe tip designs. The examples include handheld, battery-powered and/or wire free bipolar stimulation probes. The examples minimize clutter and/or time inefficiencies in an operating room due to reduction and/or elimination of wires and prevention of improper responses associated with improper nerve stimulation. The stimulation disclosed below also minimizes power consumption associated with stimulating a nerve.

In the following figures various stimulation probes are disclosed. Although the stimulation probes are primarily described as wireless devices that are capable of wirelessly communicating with a nerve integrity monitoring system, the stimulation probes (i) may be wired to a nerve integrity monitoring system, and/or (ii) may be used separate from and may not be in communication with a nerve integrity monitoring system.

Figure 1:
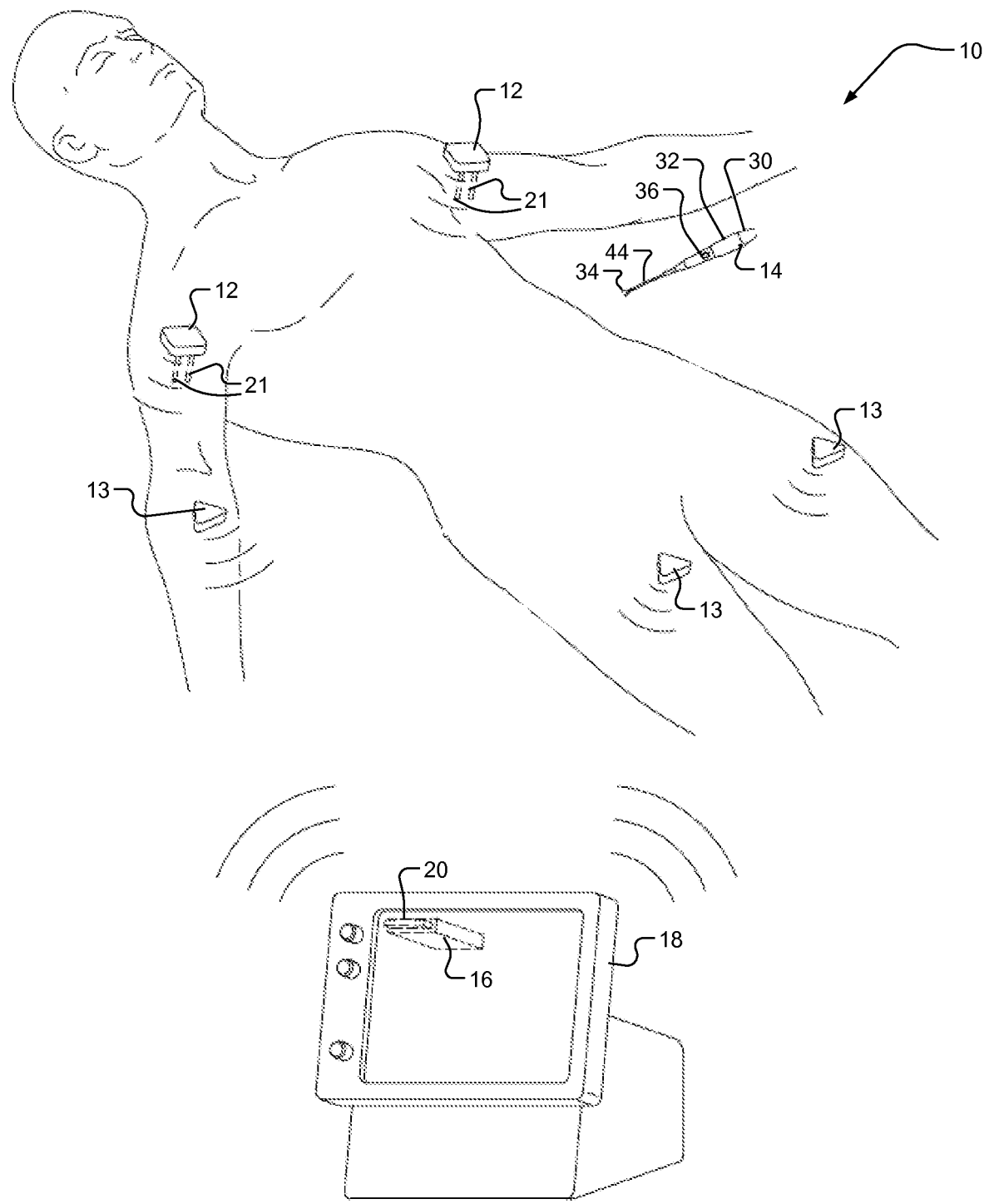
FIG. 1 is a perspective view of a wireless nerve integrity monitoring (WNIM) system including a stimulation probe in accordance with the present disclosure.

FIG. 1 shows a wireless nerve integrity monitoring (WNIM) system 10. The WNIM system 10, as shown, includes sensors 12, 13, a bipolar stimulation probe (referred to hereinafter as the "stimulation probe") 14, a wireless interface adaptor (WIA) 16 and a NIM device 18. Although a side-by-side bipolar stimulation probe is shown, the bipolar stimulation probe 14 may be a concentric or tripolar style stimulation probe that is used as a bipolar stimulation probe. Thus, electrodes of the bipolar stimulation probe may be in a side-by-side arrangement, a concentric arrangement or a tripolar arrangement. For example, a concentric stimulation probe includes an inner electrode and an outer electrode, which surrounds the inner electrode. If the inner electrode and the outer electrode are at an acute angle relative to nerve tissue, the concentric stimulation probe may be used as a bipolar stimulation probe, as the outer electrode is not perpendicular to the nerve tissue and thus is not fully in contact with the nerve tissue. As another example, if only an inner electrode and one of two outer electrodes of a tripolar probe are in contact with a nerve tissue, then the tripolar probe may be used as a bipolar probe, since the second outer electrode is not in contact with the nerve tissue.

Figure 2:
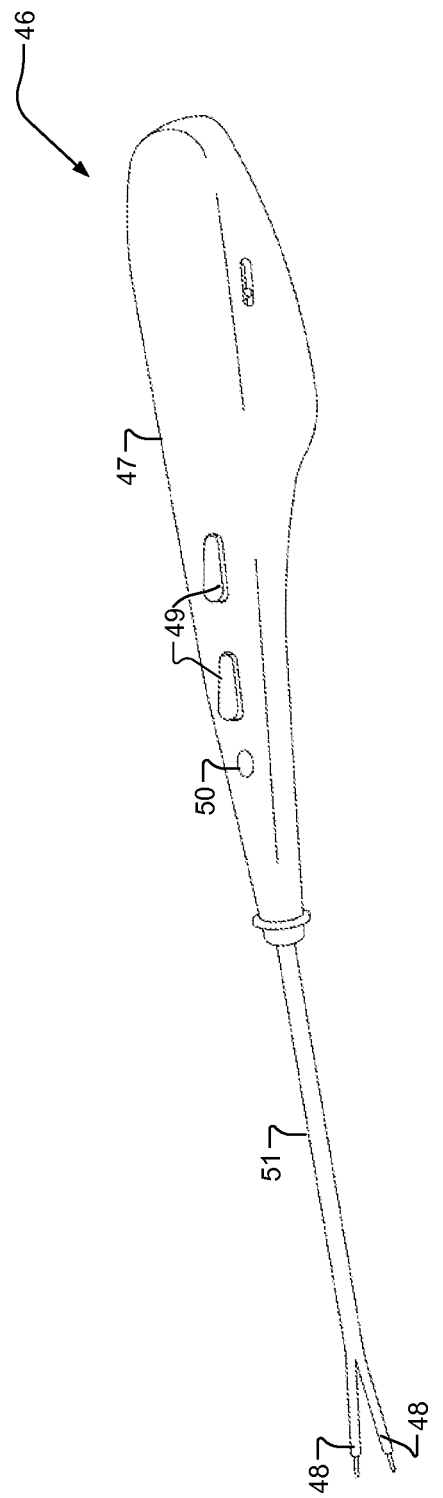
FIG. 2 is a perspective view of a stimulation probe in accordance with the present disclosure.

The WIA 16 includes a console interface module (CIM), which is shown in FIG. 2, and an interface 20 (e.g., a 32-pin connector) for connecting to the NIM device 18. The WIA 16 is shown as being plugged into a back side of the NIM device 18. Although the WIA 16 is shown as being plugged into the NIM device 18 via the interface 20, the WIA 16 may be separate from the NIM device 18 and wirelessly communicate with the NIM device 18. The sensors 12, 13 and the stimulation probe 14 wirelessly communicate with the CIM and/or the NIM device 18. In one embodiment, the WIA 16 is connected to the NIM device 18 and wirelessly communicates with the sensors 12, 13 and the stimulation probe 14. Information described below as being transmitted from the NIM device 18 to the CIM may then be relayed from the CIM to the sensors 12, 13 and/or the stimulation probe 14. Information and/or data described below as being transmitted from the sensors 12, 13 and/or the stimulation probe 14 to the CIM may then be relayed from the CIM to the NIM device 18.

The WIA 16: transfers signals between (i) the NIM device 18 and (ii) the sensors 12, 13 and the stimulation probe 14; and/or adds additional information to the signals received from the NIM device 18 prior to forwarding the signals to the sensors 12, 13 and/or stimulation probe 14, as described below. The WIA 16 may: operate essentially as a pass through device; operate as a smart device and add and/or replace information provided in received signals; and/or generate signals including determined information based on received signals. The WIA 16 allows the NIM device 18 to be compatible with legacy hardware. The WIA 16 may be unplugged from the NIM device 18 and a traditional electrode connection box may be connected to the WIA 16 using the same interface of the NIM device 18 as the WIA 16. The WIA 16 replaces cables traditionally connected between (i) a NIM device 18 and (ii) sensors 12, 13 and a stimulation probe 14. This eliminates wires traversing (extending from within to outside) a sterile field in which a patient is located.

As another example, the WIA 16 may receive signals from the sensors 12, 13 and/or the stimulation probe 14. The signals from the sensors 12, 13 and/or the stimulation probe 14 may indicate voltages, current levels, durations, amplitudes, etc. The WIA 16 may determine, for example, durations and amplitudes based on the received signals. The signals from the stimulation probe 14 may include, for example, voltages, current levels, durations, amplitudes of stimulation pulses provided to a patient. The received signals and/or the determined information may be forwarded to the NIM device 18 for evaluation and/or for display on the screen of the NIM device 18. The WIA 16 and/or the NIM device 18 may: communicate with the stimulation probe 14; control operation of the stimulation probe 14; and/or respond to the stimulation probe 14 based on the signals/parameters received from the stimulation probe 14. The WIA 16 and/or the NIM device 18 may control the number of pulses, pulse durations, direction of pulses (applied via cathodal electrode or anodal electrode), amplitudes of pulses, and/or frequency of pulses generated by the stimulation probe 14.

Although two types of sensors 12, 13 are shown in FIG. 1, other types of sensors may be incorporated in the WNIM system 10. The sensors 12 of the first type are referred to as pin sensors and include respective pairs of pins 21 (or needles) that are inserted into, for example, muscle tissue of a patient. The sensors 13 of the second type are referred to as surface sensors and are adhered to skin of a patient over, for example, muscle tissue. The pin sensors 12 may, for example, be used to detect voltage potentials between the respective pairs of pins 21 of the pin sensors 12. The surface sensors 13 may, for example, be used to detect voltage potentials between respective pads of the surface sensors 13. The pin sensors 12 may each include two pins as shown or may include a different number of pins. The pins may be referred to as electrodes. Each of the surface sensors 13 may include two or more pads. The pads may be referred to as electrodes.

The sensors 12, 13 detect electromyographic signals generated in tissue of a patient via the electrodes 34. The electromyographic signals may be in the form of voltage signals having voltage potentials. The sensors 12, 13 are used to digitize nerve and/or muscle activity and wirelessly transmit this information to the CIM and/or the NIM device 18. The sensors 12, 13 may alert the CIM and/or the NIM device 18 of bursts (e.g., increases in voltages of evoked response signals) in nerve and/or muscle activity. An evoked response signal refers to a signal generated in a tissue of a patient as a result of a stimulation signal generated by the stimulation probe 14.

Figure 3:
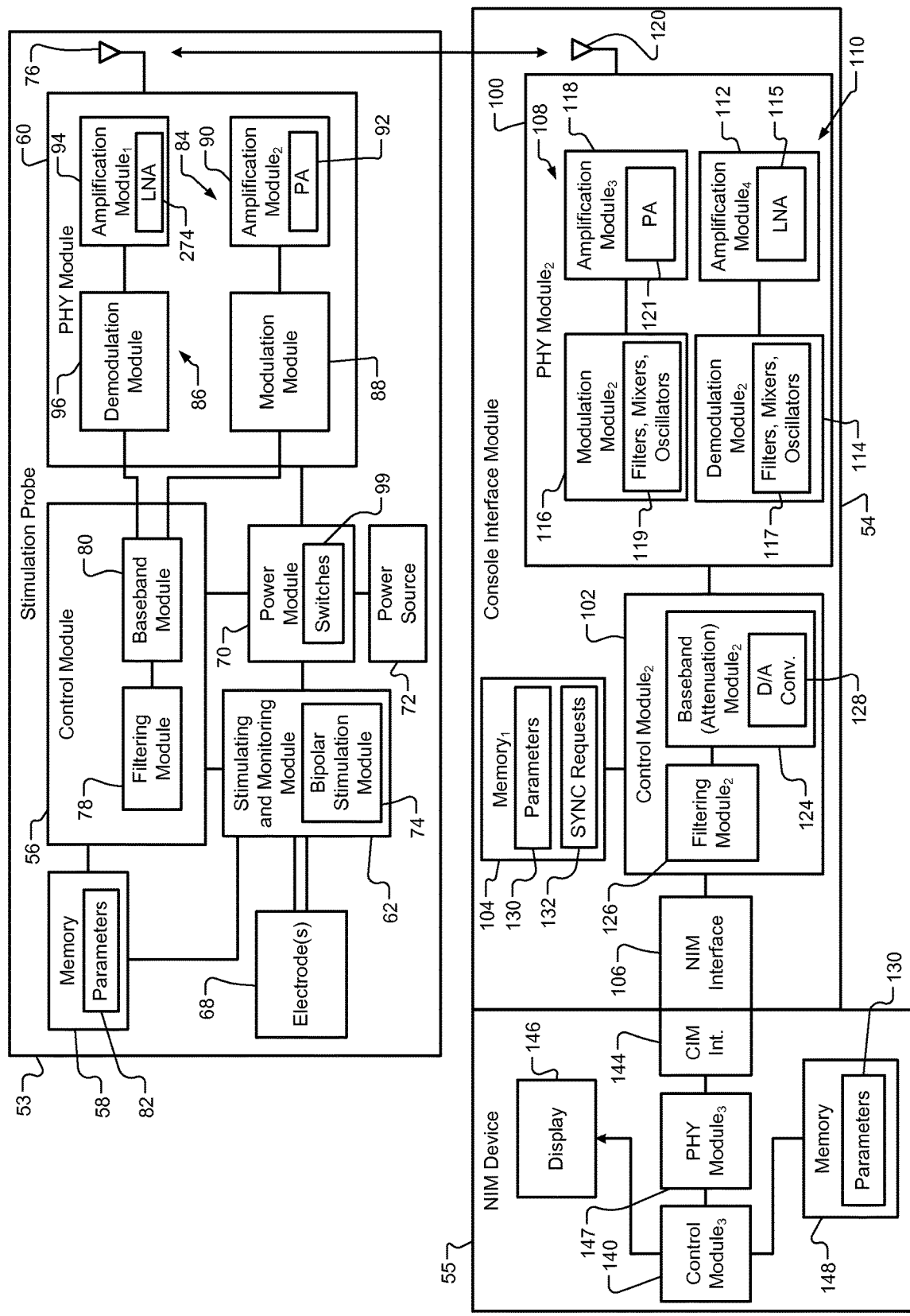
FIG. 3 is a functional block diagram of a stimulation probe, a console interface module and a NIM device in accordance with the present disclosure.
Figure 4:
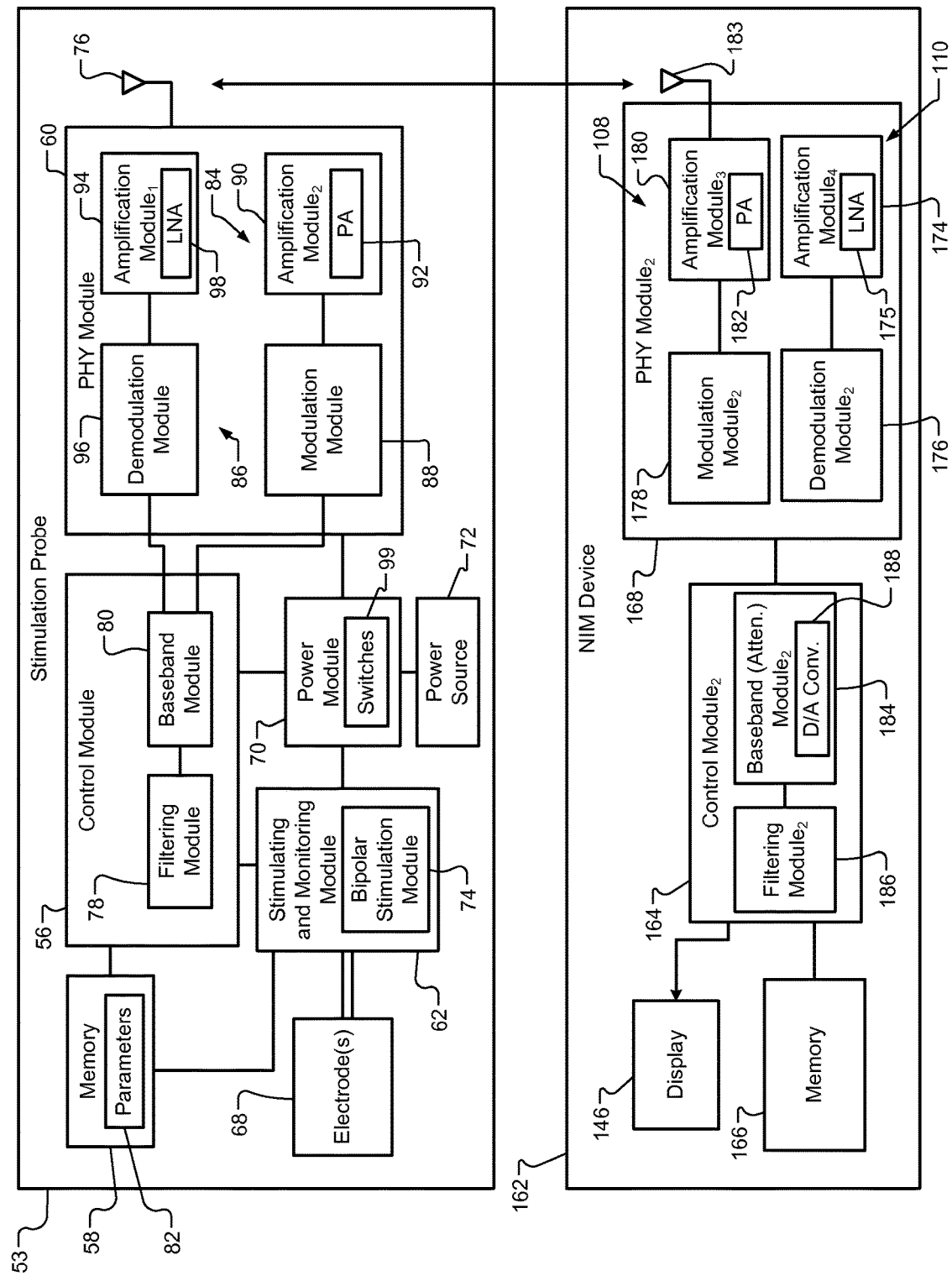
FIG. 4 is a functional block diagram of the stimulation probe of FIG. 3 and another NIM device in accordance with the present disclosure.

The stimulation probe 14 is used to stimulate nerves and/or muscle in the patient. The stimulation probe 14 includes: a housing 30 with a grip 32; two electrodes 34; one or more switches 36 (another example of which is shown in FIG. 2); and a control module (examples of which are shown in FIGS. 3-6). The electrodes 34 are separated and insulated from each other and may extend within a tube 44 to the housing 30. The switch 36 may be used to turn ON the stimulation probe 14 and/or to apply stimulation pulses to the electrodes 34. Examples of stimulation pulses are shown in FIG. 8. The stimulation pulses may be manually generated by actuating the switch 36 or may be generated via the NIM device 18 and/or the WIA 16 via the CIM. The NIM device 18 and/or the CIM may signal the control module of the stimulation probe 14 to generate stimulation pulses to stimulate one or more nerves and/or muscles in proximity of the electrodes 34. Voltage potentials between the electrodes 34 may be determined by: the control module of stimulation probe 14; a control module of the NIM device 18 (examples of which are shown in FIGS. 3-4); and/or a control module of the CIM (an example of which are shown in FIG. 3).

The stimulation probe 14 may wirelessly transmit information to the CIM and/or NIM device 18. The information may include: timing information; voltage potentials between the electrodes 34; number of stimulation pulses; pulse identifiers (IDs); voltages and current levels of stimulation pulses generated; and amplitudes, peak magnitudes and/or durations of stimulation pulses generated. The timing information may include: start and end times of stimulation pulses; durations of stimulation pulses; time between stimulation pulses of different electrodes; and/or time between stimulation pulses of the same electrode.

In another embodiment, the WIA 16 is not included in the WNIM system 10. In this embodiment, the NIM device 18 wirelessly communicates directly with the sensors 12, 13 and the stimulation probe 14. This may include communication with the sensors 12, 13 and the stimulation probe 14 shown in FIG. 1 and/or communication with other sensors and/or stimulation devices. The WNIM system 10 may include any number of sensors and/or stimulation probes.

Referring now also to FIG. 2, which shows a stimulation probe 46, which may replace the stimulation probe 14 of FIG. 1. Although a side-by-side bipolar stimulation probe is shown, the bipolar stimulation probe 46 may be a concentric or tripolar style stimulation probe that is used as a bipolar stimulation probe. The stimulation probe 46 includes a housing 47; two electrodes 48; switches 49; a light 50, and a control module (examples of which are shown in FIGS. 3-6). The electrodes 48 are separated and insulated from each other and may extend within a tube 51 to the housing 47. The switches 49 may be used to turn ON the stimulation probe 14 and/or to apply stimulation pulses to the electrodes 48. The switches 49 may also be used to increase (or increment) or decrease (or decrement) amounts of current supplied to the electrodes 48 during stimulation. The stimulation probe 46 may also include visual and/or audible alerts (e.g., via the light 50) to indicate when the electrodes are contacting and/or supplying current to tissue. As an example, the light 50 may blink and/or change color based on whether the electrodes 48 are contacting and/or supplying current to tissue. Examples of stimulation pulses that may be provided by the stimulation probe 46 are shown in FIG. 8. The stimulation pulses may be manually generated by actuating one or more of the switches 49 or may be generated via the NIM device 18 and/or the WIA 16 via the CIM. The NIM device 18 and/or the CIM may signal the control module of the stimulation probe 14 to generate stimulation pulses to stimulate one or more nerves and/or muscles in proximity of the electrodes 34.

Referring now to FIG. 1 and FIG. 3, which shows a stimulation probe 53, a CIM 54 and a NIM device 55. The stimulation probe 53 may wirelessly communicate with the CIM 54 and/or with the NIM device 55 via the CIM 54. The stimulation probe 53 may replace and/or operate similar to any of the stimulation probes 14 and 46 described above. The CIM 54 may be included in the WIA 16 of FIG. 1.

The stimulation probe 53 includes a control module 56 (e.g., a microprocessor), a memory 58, a physical layer (PHY) module 60 (e.g., a transceiver and/or radio), a stimulating and monitoring module 62, electrodes 68, a power module 70, and a power source 72. The electrodes 68 may be connected to and/or include tips of the stimulation probe 53. The stimulating and monitoring module 62 receives power from the power module 72 and generates stimulation signals via the electrodes 68, which are in contact with and/or supply current to tissue of a patient. Although the modules 60, 62, 70 are shown as being separate from the control module 56, one or more of the modules 60, 62, 70 or portions thereof may be incorporated in the control module 56. Although the electrodes 68 are shown as being within the stimulation probe 53, the electrodes 68: may extend from the stimulation probe 53; may directly contact tissue of a patient; and/or may be connected to a surgical tool (see for example FIGS. 5, 9 and 10) and indirectly supply current to the tissue via the tool. The tools disclosed herein may be referred to as surgical tools. A surgical tool may be any tool used during surgery, such as forceps, tweezers, pliers, clamps, etc. and/or other tools disclosed herein.

The stimulating and monitoring module 62 may detect a voltage supplied to the electrodes 68 and/or voltage potentials applied across two of the electrodes 68 and generate stimulation information signals indicating the same. The stimulating and monitoring module 62 (i) measures current supplied to one or more of the electrodes 68, and (ii) generates a stimulation information signal indicating the same. The stimulation information signals may be provided to the control module 56.

The stimulating and monitoring module 62 includes a bipolar stimulation module 74 that alternates states of the electrodes 68. The bipolar stimulation module 74 changes states of the electrodes 68 between anode and cathode states. For example, during a first mode and generation of a first pulse, a first one of the electrodes 68 may operate as an anode and a second one of the electrodes 68 may operate as a cathode. During a second mode and generation of a second pulse, the first electrode may operate as a cathode and the second electrode may operate as an anode. Use of electrical switching to alternate the physical connection of the anode and cathode to tips of the stimulation probe 53, allows for generation of dual pulses in dual directions, where each pulse has a same polarity. For example, both pulses may have a positive polarity (e.g., 5V) or both pulses may have a negative polarity (−5V). This allows for use of a single power source having and/or supplying a single output voltage with a single polarity. The electrical switching between modes/electrode states may be timed by the control module 56. The switching is further described below with respect to FIGS. 6-8. As a result of the switching between anode and cathode states and the generation of dual pulses in dual directions on a nerve, the nerve action potential is not dependent upon: orientation of the stimulation probe 53 in a hand of a surgeon; and/or anatomical variation of a nerve (or orientation of the nerve). The need to orient a cathode distally along a nerve is eliminated, as a pulse is sent in both distal and proximal directions along a nerve. Cathodal orientation of the stimulation probe 53 is electrically alternated to ensure that a nerve receives a cathodal stimulation pulse.

The control module 56 wirelessly communicates with the CIM 54 and/or one or more of the NIM device 55 via the PHY module 60 and an antenna 76. The control module 56 includes a filtering module 78 and a BB module 80. The filtering module 78 may operate as a bandpass filter and filter out frequencies of the amplified signals outside of a predetermined frequency range and a direct current (DC) voltage. This can eliminate and/or minimize noise, such as 60 Hz noise. The filtering module 78 may receive stimulation information signals from the stimulating and monitoring module 62 and convert the stimulation information signals and/or signals generated based on the stimulation information signal to BB signals. The stimulating and monitoring module 62 may monitor and indicate to the control module 56 actual voltages, current levels, amplitudes, and durations of stimulation pulses via the stimulation information signals. The control module 56 may then transmit this information via the PHY module 60 to the CIM 54 and/or the NIM device 55.

The BB module 80 may include an analog-to-digital (A/D) converter and convert the BB signals from the filtering module 78 to digital BB signals. The BB module 80 and/or the A/D converter may sample the output of the filtering module 78 at a predetermined rate to generate frames, which are included in the digital BB signal. The BB module 80 may then upconvert the digital BB signal to an intermediate frequency (IF) signal. The BB module 80 may perform DSSS modulation during upconversion from the digital BB signal to the IF signal. The BB module 80 may include a mixer and oscillator for upconversion purposes. The BB module 80 and/or the control module 56 may compress and/or encrypt BB signals transmitted to the PHY module 60 prior to upconverting to IF signals and/or may decompress and/or decrypt signals received from the PHY module 60.

The memory 58 is accessed by the control module 56 and stores, for example, parameters 82. The parameters 82 may include parameters associated with stimulation pulses generated via the electrodes 68. The parameters associated with stimulation pulses may include voltages, wavelengths, current levels, amplitudes, peak magnitudes, pulse durations, etc.

The PHY module 60 includes a transmit path 84 (or transmitter) and a receiver path 86 (or receiver). The transmit path 84 includes a modulation module 88 and an amplification module 90. The modulation module 88 modulates the IF signal to upconvert the IF signal to a RF signal. This may include GFSK modulation. The modulation module 88 may include, for example, a filter, a mixer, and an oscillator. The amplification module 90 may include a power amplifier 92, which amplifies the RF signal and transmits the RF signal via the antenna 76.

The receiver path 86 includes a second amplification module 94 and a demodulation module 96. The second amplification module 94 may include a LNA 98. The second amplification module 94 amplifies RF signals received from the CIM. The demodulation module 96 demodulates the amplified RF signals to generate IF signals. The IF signals are provided to the BB module 80, which then downconverts the IF signals to BB signals.

The power module 70 receives power from the power source 72 and supplies the power to the stimulating and monitoring module 62, the control module 56 and the PHY module 60. The power module 70 may include switches 99. The switches 99 may be actuated to generate stimulation pulses. When the switches 99 are closed or toggled and/or when the control module 56 generates a control signal commanding generation of one or more stimulation pulses, the power module 70 and/or the control module 56 signals the stimulating and monitoring module 62 to generate the one or more stimulation pulses. The timing, amplitude, and/or duration of each of the stimulation pulses may be based on information received from the CIM 54 and/or the NIM device 55. Frequency of the stimulation pulses and/or time between the stimulation pulses may also be controlled and based on corresponding information received from the CIM 54 and/or the NIM device 55. The stimulation probe 53 may be synchronized with the CIM 54 and/or NIM device 55. Synchronization (SYNC) requests 132, shown as being stored in the memory 104, may be transmitted between (i) the stimulation probe 53 and (ii) the CIM 54 and NIM 55. The CIM 54 and/or NIM 55 may generate command signals indicating to the stimulation probe 53 when to generate the stimulation pulses and based on this timing may monitor responses detected by sensors (e.g., sensors 12, 13 of FIG. 1). As an alternative, the stimulation probe 53 may transmit signals to the CIM 54 and/or the NIM 55 indicating when the stimulation pulses have and/or are to be generated. In this way, stimulation pulse generation is synchronized with the detected responses. This allows the CIM 54 and/or the NIM 55 to and/or a surgeon to relate responses with respective stimulation pulses, which prevents responses and/or artifacts associated with a first stimulation pulse to not be confused as being a result of other stimulation pulses. This can also prevent confusion between stimulation pulses responses and electromyography (EMG) signals and thus prevent false positives. This is unlike a wireless stimulation probe that does not wirelessly communicate with a CIM and/or a NIM. As described below, the CIM 54 and/or the NIM 55 may filter out artifacts, responses and/or EMG signals outside of predetermined and/or selected monitoring periods. The monitoring periods correspond respectively to the stimulation pulses and occur subsequent to when the stimulation pulses are generated.

The CIM 54 includes a PHY module 100, a control module 102, the memory 104, and a NIM interface 106 (e.g., 32 pin connector). The PHY module 100 includes a receive path (or receiver) 108 and a transmit path (or transmitter) 110. The receive path 108 includes an amplification module 112 and a demodulation module 114. The amplification module 112 amplifies RF signals received from the stimulation probe 53 and/or from the sensor 12, 13. The amplification module 112 may include a LNA 115. The demodulation module 114 demodulates and downconverts the amplified RF signals to generate IF signals. The demodulation module 114 may include a filter, mixer, and an oscillator (collectively referred to as 117). The transmit path 110 includes a modulation module 116 and an amplification module 118. The modulation module 116 modulates and upconverts IF signals from the control module 102 to generate RF signals. This may include Gaussian frequency-shift keying (GFSK) modulation. The modulation module 116 may include, for example, a filter, a mixer, and an oscillator (collectively identified as 119). The amplification module 118 transmits the RF signals to the stimulation probe 53 via an antenna 120. The amplification module 118 may include a power amplifier 121.

The control module 102 includes a BB module 124 and a filtering module 126. The BB module 124 converts IF signals received from the PHY module 100 to BB signals and forwards the BB signals to the filtering module 126. The BB module 124 also converts BB signals from the filtering module 126 to IF signals, which are forwarded to the modulation module 116. The BB module 124 may include a D/A converting module 128. The D/A converting module 128 may include an A/D converter to convert analog signals from the filtering module 126 to digital signals. The D/A converting module 128 may include a D/A converter to convert digital signals from the PHY module 100 to analog signals. In one embodiment, the BB module 124 does not include the D/A converting module 128 and digital signals are passed between the filtering module 126 and the PHY module 100. The BB module 124 may attenuate signals received from the demodulation module 114 to have amplitudes similar to amplitudes of signals received at the gain module 63 and/or the filtering module 64 of the stimulation probe 53.

The filtering module 126 may be a bandpass filter and remove frequencies of signals outside a predetermined range and/or DC signals. This can eliminate and/or minimize noise, such as 60 Hz noise. The BB module 124 and/or the control module 102 may compress and/or encrypt signals transmitted to the modulation module 116 and/or decompress and/or decrypt signals received from the demodulation module 114. Although the CIM 54 is shown as being connected to the NIM device 55 via the NIM interface 106, the CIM 54 may be separate from the NIM device 55 and wirelessly communicate with the NIM device 55 via the PHY module 100.

The memory 104 is accessed by the control module 102 and stores, for example, parameters 130. The parameters 130 may include parameters associated with generation of stimulation pulses, as described above. The parameters 130 may include voltages, current levels, amplitudes, peak magnitudes, pulse durations, etc. and may include or be the same as the parameters 82.

The NIM device 55 may include a control module 140, a PHY module 142, a CIM interface 144, a display 146 and a memory 148. The control module 140: sends request signals to and receives information from the stimulation probe 53 and/or the sensors 12, 13 via the CIM 54; and displays electromyographic signals and/or other related information on the display 146. The PHY module 142 may transmit signals to and receive signals from the control module 140 via the interfaces 106, 144 as shown or wirelessly via an antenna (not shown). The memory 148 is accessed by the control module 140 and stores the parameters 130.

The control modules 56, 102, the BB modules 80, 128, the PHY modules 60, 100, and/or one or more modules thereof control timing of signals transmitted between the stimulation probe 53 and the CIM 54. The PHY modules 60, 100 may communicate with each other in a predetermined frequency range. As an example, the PHY modules 60, 100 may communicate with each other in 2.0-3.0 giga-hertz (GHz) range. In one embodiment, the PHY modules 60, 100 transmit signals in a 2.4-2.5 GHz range. The PHY modules 60, 100 may communicate with each other via one or more channels. The PHY modules 60, 100 may transmit data at predetermined rates (e.g., 2 mega-bits per second (Mbps)).

Referring now to FIGS. 1 and FIG. 4, which shows the stimulation probe 53 and a NIM device 162. The stimulation probe 53 may communicate directly with the NIM device 162. The stimulation probe 53 includes the control module 56, the memory 58, the PHY module 60, the stimulating and monitoring module 62, the electrodes 68, the power module 70, the power source 72, and the antenna 76. The control module 56 includes the filtering module 78 and the baseband module 80. The memory 58 stores the parameters 82. The stimulating and monitoring module 62 includes the bipolar stimulation module 74. The power module 70 includes the switches 99. The PHY module 60 includes the paths 84, 86 and the modules 88, 92, 94, 96.

The NIM device 162 includes a control module 164, a memory 166, a PHY module 168, and the display 146. Functionality of the CIM 54 of FIG. 2 is included in the NIM device 162. The PHY module 168 includes a receive path 170 (or receiver) and a transmit path 172 (or transmitter). The receive path 170 includes an amplification module 174 and a demodulation module 176. The amplification module 174, via a LNA 175, amplifies RF signals received from the stimulation probe 53 and/or from sensors 12, 13. The demodulation module 176 demodulates and downconverts the amplified RF signals to generate IF signals. The transmit path 172 includes a modulation module 178 and an amplification module 180. The modulation module 178 and the amplification module 180 may operate similar to the modulation module 116 and the amplification module 118. The amplification module 118 may include a power amplifier 182 and transmits RF signals via an antenna 183 to the stimulation probe 53 and/or from sensors 12, 13.

The control module 164 includes a BB module 184 and a filtering module 186. The BB module 184 converts IF signals received from the PHY module 168 to BB signals and forwards the BB signals to the filtering module 186. The BB module 184 also converts BB signals from the filtering module 186 to IF signals, which are forwarded to the modulation module 178. The BB module 184 may include a D/A converting module 188. The D/A converting module 188 may include an A/D converter to convert analog signals from the filtering module 186 to digital signals. The D/A converting module 188 may include a D/A converter to convert digital signals from the PHY module 168 to analog signals. In one embodiment, the BB module 184 does not include the D/A converting module 188 and digital signals are passed between the filtering module 186 and the PHY module 168. The BB module 184 may attenuate signals received from the demodulation module 176 to have amplitudes similar to amplitudes of signals received at the gain module 63 and/or the filtering module 64 of the stimulation probe 53. The filtering module 186 may be a bandpass filter and remove frequencies of signals outside a predetermined range and/or DC signals. This can eliminate and/or minimize noise, such as 60 Hz noise. The BB module 184 and/or the control module 164 may compress and/or encrypt signals transmitted to the modulation module 178 and/or decompress and/or decrypt signals received from the demodulation module 176.

The filtering modules 126, 186 of the CIM 54 and the NIM 162 of FIGS. 3-4 may filter out artifacts, responses and/or EMG signals outside of predetermined and/or selected monitoring periods. The monitoring periods correspond respectively to stimulation pulses generated by a stimulation probe and occur subsequent to when the stimulation pulses are generated. As an example, the filtering modules 126, 186 may set an adjustable rejection period that begins when a stimulation pulse is generated and extends past a period when a stimulus artifact occurs as a result of the stimulation pulse. Traces monitored subsequent to the rejection period and during the corresponding monitoring period are then monitored, which allows any electronic noise caused by the stimulation pulse to settle prior to reading EMG data. The monitoring period may begin when the rejection period ends. Each of the rejection periods and each of the monitoring periods may correspond to one or more stimulation pulses. Each of the rejection periods may include one or more periods during which one or more of the stimulation pulses are generated. Each of the monitoring periods may be subsequent to one or more stimulation pulses. If one or more series of stimulation pulses are provided, a rejection period may begin at a beginning of a first stimulation pulse in a first series and end (i) subsequent to a last stimulation pulse in the first series, or (ii) subsequent to a last stimulation pulse in a second or higher numbered series.

Figure 5:
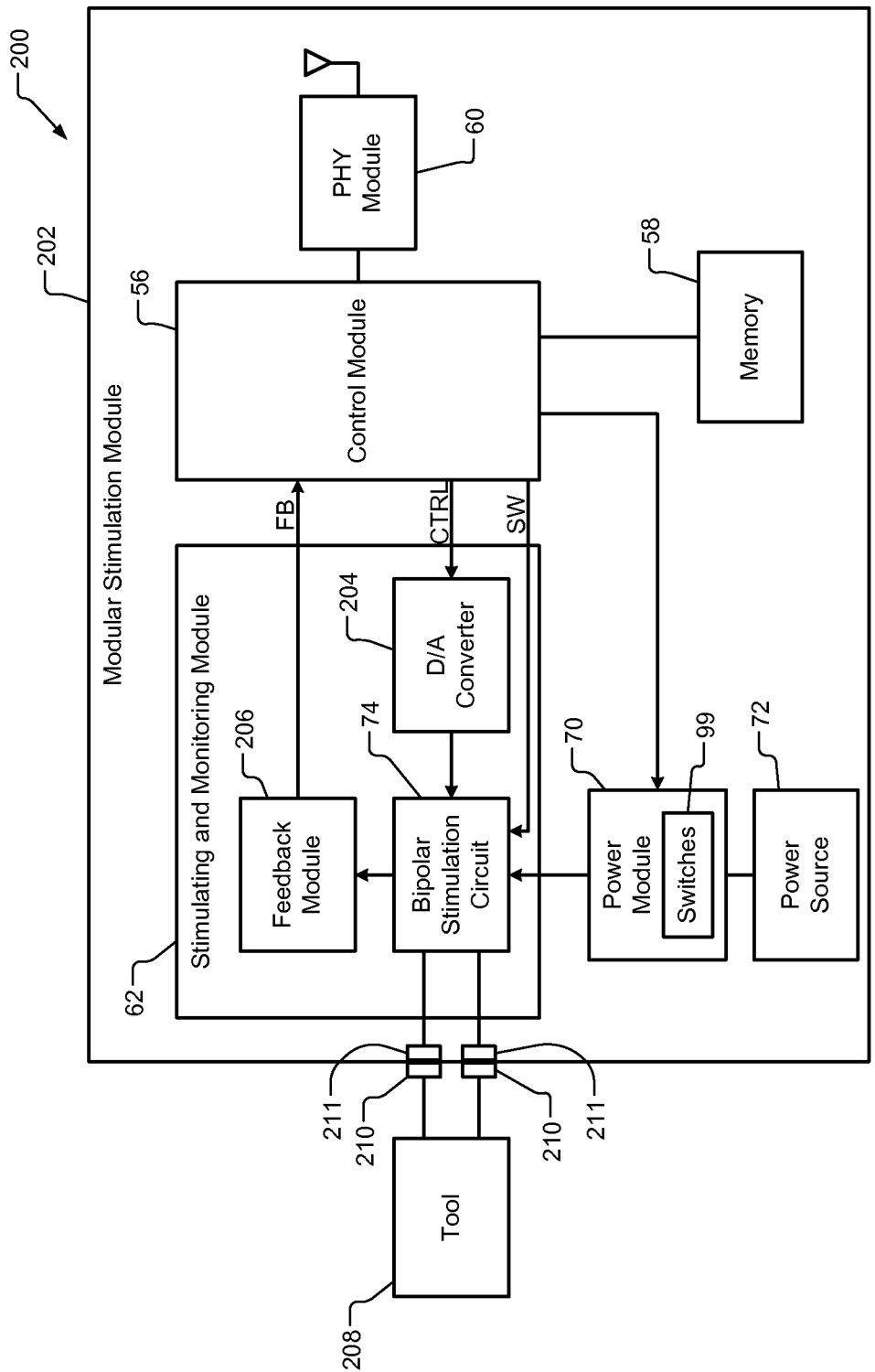
FIG. 5 is a functional block diagram of a portion of the stimulation probe of FIG. 3 including a modular stimulation module in accordance with the present disclosure.

FIG. 5 shows a portion 200 of the stimulation probe 53 including a modular stimulation module 202. The modular stimulation module 202 includes the memory 58, the control module 56, the PHY module 60, the stimulating and monitoring module 62, the power module 70 and the power source 72. The stimulating and monitoring module 62 includes the bipolar stimulation module 74, a digital-to-analog (D/A) converter 204, and a feedback module 206. The power module 70 includes the switches 99. The D/A converter 204 (i) receives a control signal CTRL from the control module 56, and (ii) converts the control signal from a digital signal to an analog signal. The control signal may include and/or be indicative of an amount of current to be applied via the electrodes 68. The amount of current supplied from the control module 56 to the D/A converter 204 may be proportional to an amount of current actually supplied to the electrodes 68. The control signal CTRL may be generated based on a request signal received from one of the NIM devices 55, 162 and/or the CIM 54 of FIGS. 3-4. As an alternative to the control module 56 supplying current to the D/A converter 204, the control module 56 may control the power module 70 to supply the current to the D/A converter 204.

In operation, the bipolar stimulation module 74 generates pulses based on an output of the D/A converter 204 and a switch control signal SW from the control module 56. The switch control signal SW changes states of switches in the bipolar stimulation module 74, such that two pulses are provided in opposite directions along a nerve and/or nerve tissue. The feedback module 206 (i) monitors current supplied to the electrodes 68, and (ii) generates a feedback signal FB, which is provided to the control module 56. The control module 56 may then, based on the feedback signal, adjust pulses (e.g., change pulse voltages, current levels, amplitudes, durations, timing, etc.) generated by the stimulation probe 200 and/or to alter states of switches in the bipolar stimulation module 74. The feedback signal FB may be transmitted from the PHY module 60 to one of the NIM devices 55, 162 and/or the CIM 54 of FIGS. 3-4. One of the NIM devices 55, 162 and/or the CIM 54 may then transmit a request signal to the control module 56 to adjust pulses (e.g., change pulse voltages, current levels, amplitudes, durations, timing, etc.) generated by the stimulation probe 200 and/or to alter states of switches in the bipolar stimulation module 74. Information associated with the feedback signal FB may be stored in the memory 58 and accessed by the control module 56.

The electrodes 68 may be connected to a tool 208 via connectors 210, 211 (may be referred to as connecting elements). The connectors 210 connect to the connectors 211. Some examples of the tool 208 are shown in FIGS. 9-19E. The tool 208 may be, for example, forceps, a clamp, a scissors, pliers, spreaders, or other tool having two electrical contact points for contacting tissue of a patient. The electrodes 68 may be within and/or extend from the modular stimulating module 202. If the electrodes 68 are within the modular stimulating module, the electrodes may be in the form of conductors, traces, or other suitable electrically conductive element to provide current to and/or receive current from the tool 208. If the electrodes 68 extend from the modular stimulating module 202, the electrodes 68 may be in the form of pins, connectors, wires, etc. Since dual pulses are generated in dual directions (anodal and cathodal directions) via the electrodes 68, polarity indicators do not need to be provided on the electrodes 68. This is different than a traditional bipolar stimulation probe, which typically includes a polarity marker on a cathodal electrode to visibly indicate to a surgeon that the electrode operates as a cathode.

Figure 6:
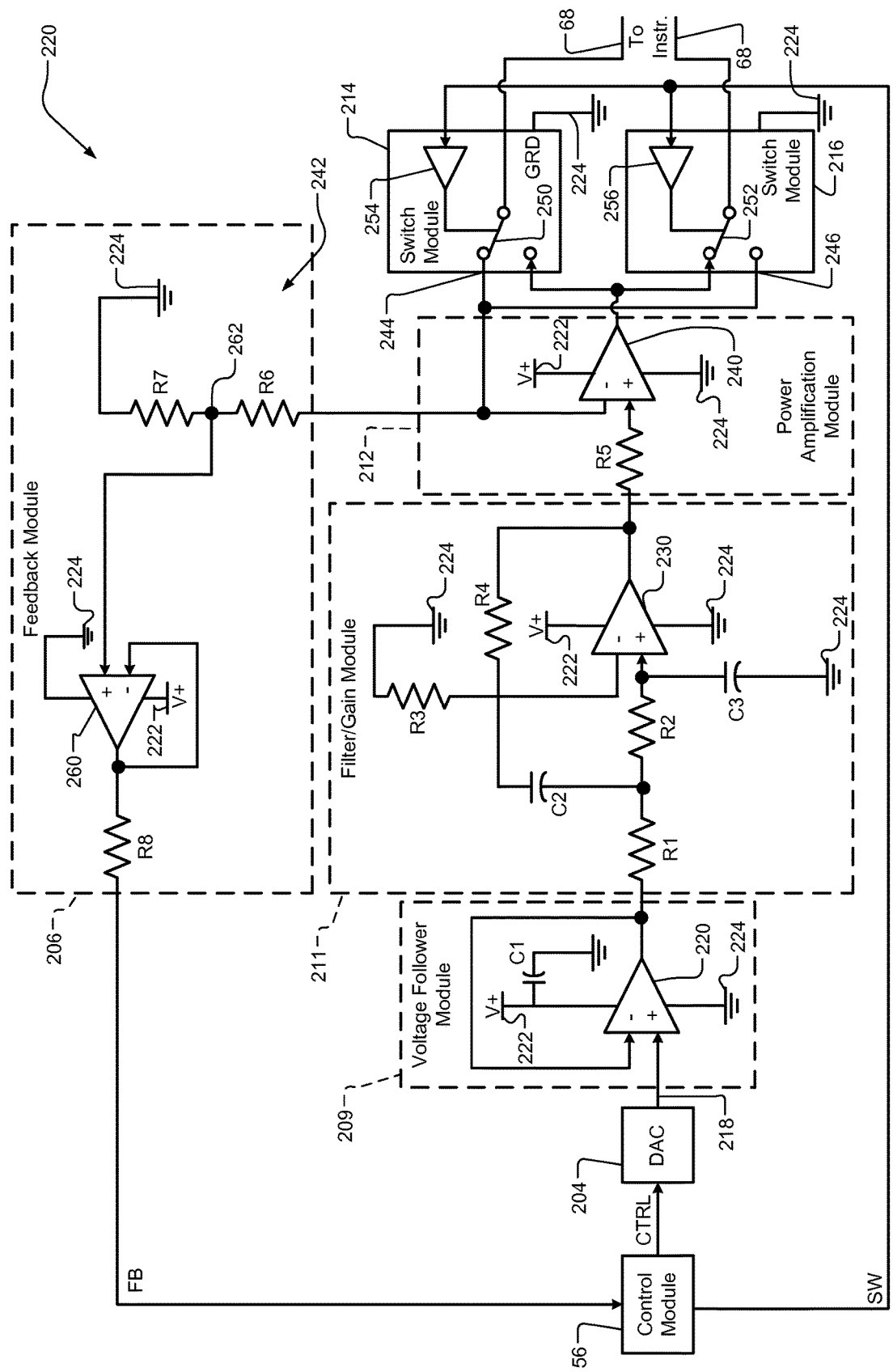
FIG. 6 is a functional block and schematic diagram of a portion of the modular stimulation module in accordance with the present disclosure.

FIG. 6 shows an example of a portion 220 of the modular stimulation module 202 of FIG. 5. The portion 220 includes the control module 56, the D/A converter 204, the feedback module 206, a voltage follower module 209, a filter/gain module 211, a power amplification module 212, and switch modules 214, 216. The control module 56 generates the control signal CTRL, the switch control signal SW and receives from the feedback module 206 the feedback signal FB. The D/A converter 204 converts the control signal CTRL to a command signal 218.

The voltage follower module 209 includes a first operational amplifier 220 and a first capacitance C1. The first operational amplifier 220 includes a non-inverting input and an inverting input. The non-inverting input is connected to and receives an output of the D/A converter 204. The inverting input is connected to an output of the first operational amplifier 220. A voltage at an output of the voltage follower module 209 is proportional to a voltage at the non-inverting input of the first operational amplifier 220. The first operational amplifier 220 receives power from a power terminal 222 and is connected to a ground or reference terminal 224. The power terminal 222 is connected to the capacitance C1, which is connected to the reference terminal 224.

The filter/gain module 211 includes: resistances R1, R2, R3, R4; capacitances C2, C3; and a second operational amplifier 230 with a non-inverting input and an inverting input. The resistances R1, R2 are connected in series between the output of the first operational amplifier 220 and the non-inverting input of the second operational amplifier 230. The second capacitance C2 and the resistance R4 are connected in series between (i) a connection point between the resistances R1 and R2 and (ii) an output of the second operational amplifier 230. The capacitance C3 is connected between the non-inverting input of the second operational amplifier 230 and the reference terminal 224. The resistance R3 is connected between the inverting input of the second operational amplifier 230 and the reference terminal 224. The second operational amplifier 230 receives power from the power terminal 222 and is connected to the reference terminal 224.

The power amplification module 212 includes a resistance R5 and a third operational amplifier 240. The resistance R5 is connected between the output of the second operational amplifier 230 and a non-inverting input of the third operational amplifier 240. An inverting input of the third operational amplifier 240 is connected to a voltage divider 242 and to feedback outputs 244, 246 of the switch modules 214, 216. The third operational amplifier 240 may be configured as a transconductance amplifier as shown or a voltage amplifier such that the third operational amplifier 240 performs a voltage to current converter. The third operational amplifier 240 receives power from the power terminal 222 and is connected to the reference terminal 224.

The switch modules 214, 216 include respective switches 250, 252 and buffers 254, 256. Each of the switches 250, 252 includes a first terminal, a center terminal, and a second terminal. The center terminals are connected respectively to the electrodes 68. The first terminals of the switches 250, 252 are connected to the inverting input of the third operational amplifier 240 and the voltage divider 242. The second terminals of the switches 250, 252 are connected to each other and to an output of the third operational amplifier 240. The switches 250, 252 are controlled via the switch control signal SW, which is provided to both of the switches via the buffers 254, 256. The switch control signal SW changes states of the switches between being connected to (i) the inverting input of the third operational amplifier 240 and the voltage divider 242 and (ii) the output of the third operational amplifier 240. At any instance in time, only one of the first terminals of the switches 250, 252 is connected to the inverting input of the third operational amplifier 240 and the voltage divider 242. At any instance in time, only one of the first terminals of the switches 250, 252 is connected to the output of the third operational amplifier 240. As a result while current is supplied via one of the switches 250, 252 to one of the electrodes 68, current is received by the other one of the electrodes 68 and provided via the other one of the switches 250, 252 to the inverting input of the third operational amplifier 240 and the voltage divider 242.

The feedback module 206 may include: the voltage 242 with resistances R6, R7; a fourth operational amplifier 260; and resistance R8. The resistances R6, R7 are connected in series between the inverting input of the third operational amplifier 240 and the reference terminal 224. A center terminal 262 between the resistances R6 and R7 is connected to a non-inverting input of the fourth operational amplifier 260. An output of the fourth operational amplifier 260 is connected to an inverting input of the fourth operational amplifier 260. The fourth operational amplifier 260 receives power from the power terminal 222 and is connected to the reference terminal 224. The fourth operational amplifier 260 may be configured as a transconductance amplifier as shown such that the fourth operational amplifier 260 performs a voltage to current converter. The resistance R8 is connected between the output of the fourth operational amplifier 260 and the control module 56.

Figure 7:
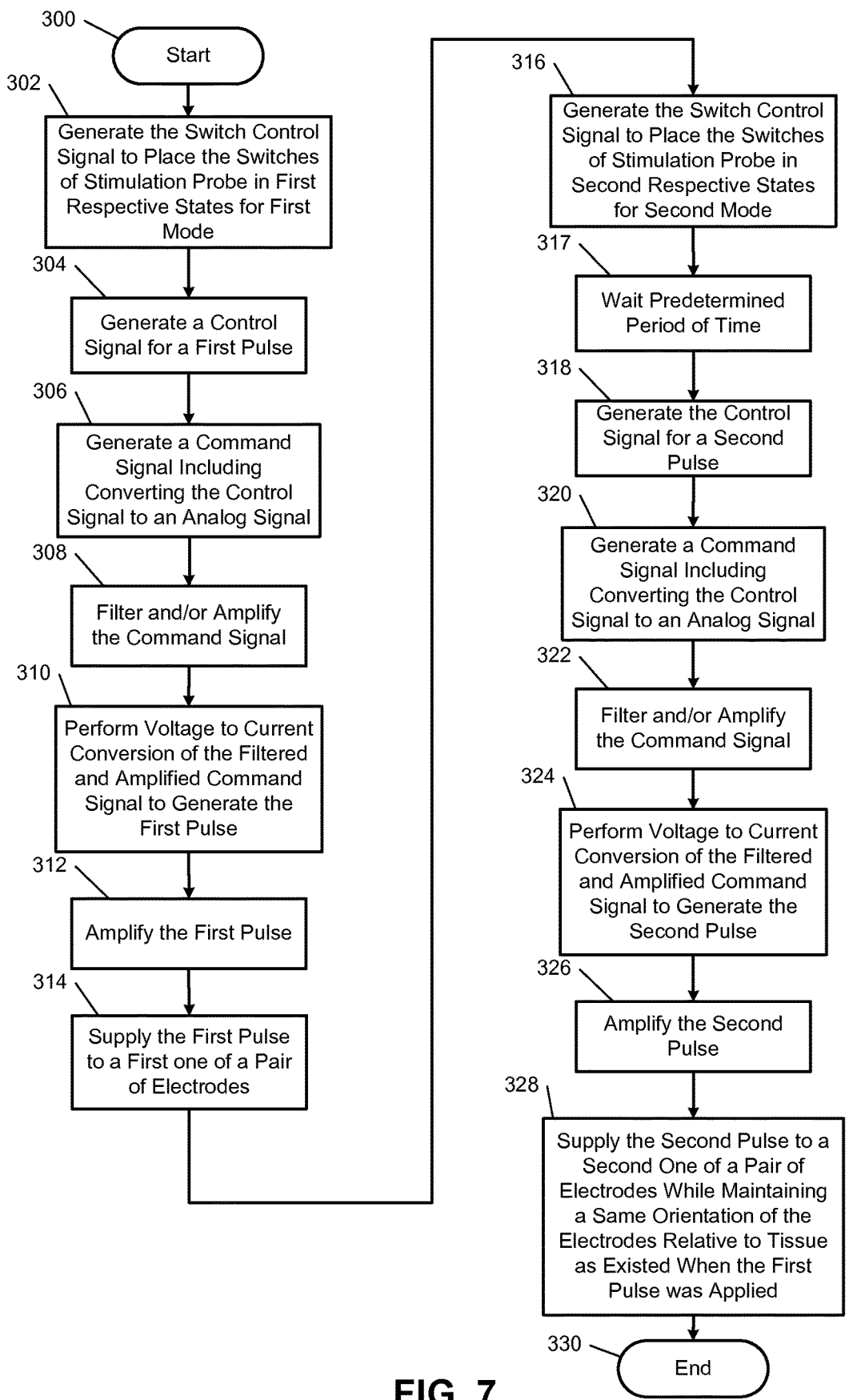
FIG. 7 illustrates a method of operating a stimulation probe in accordance with the present disclosure.

The systems, devices and modules disclosed herein may be operated using numerous methods, an example method is illustrated in FIG. 7. In FIG. 7, a method of operating a stimulation probe is shown. Although the following tasks are primarily described with respect to the implementations of FIGS. 1-6, the tasks may be easily modified to apply to other implementations of the present disclosure. The tasks may be iteratively performed.

The method may begin at 300. At 302, the control module 56 generates the switch control signal SW to place the switches 250, 252 in first respective states for the first mode. At 304, the control module 56 generates the control signal CTRL for a first pulse. The control module 56 in generating the control signal CTRL controls amplitude and duration of the first pulse. The control signal CTRL includes a voltage based version of the first pulse.

At 306, the D/A converter 204 converts the control signal CTRL to the command signal 218. At 308, the filter/gain module 211 filters and/or amplifies the command signal 218 and/or output of the voltage follower module 209.

At 310, the power amplification module 212 amplifies and performs a voltage to current conversion of an output of the filter/gain module 211. At 312, current out of the power amplification module 212 is provided to switch 250. An example of the first pulse 311 is shown in FIG. 8. Although the first pulse is shown having a certain amplitude and duration, the first pulse may have a different amplitude and duration. At 314, the first pulse is supplied from the switch 250 to the first one of the electrodes 68 and/or first tip (TIP A in FIG. 8).

At 316, the control module 56 generates the switch control signal SW to place the switches 250, 252 in second respective states for the second mode. At 317, the control module 56 may wait a predetermined period of time (e.g., 100-300 micro-seconds) before proceeding to task 318. This accounts for a refractory period of the nerve tissue that may occur subsequent to the applying of the first pulse. At 318, the control module 56 generates the control signal CTRL for a second pulse after lapse of the predetermined period. The control module 56 in generating the control signal CTRL controls amplitude and duration of the second pulse. The control signal CTRL includes a voltage based version of the second pulse.

At 320, the D/A converter 204 converts the control signal CTRL to the command signal 218. At 322, the filter/gain module 211 filters and/or amplifies the command signal 218 and/or output of the voltage follower module 209.

At 324, the power amplification module 212 amplifies and performs a voltage to current conversion of an output of the filter/gain module 211. At 326, current out of the power amplification module 212 is provided to switch 252. An example of the second pulse 325 is shown in FIG. 8. Although the second pulse is shown having a certain amplitude and duration, the second pulse may have a different amplitude and duration. At 328, the second pulse is supplied from the switch 252 to the second one of the electrodes 68 and/or second tip (TIP B in FIG. 8). The first pulse and the second pulse output at 314, 328 are monophasic.

As a result of the dual pulses provided to the nerve tissue via the above method, electromyographic signals may be generated and detected by, for example, the sensors 12, 13 of FIG. 1. The method may end at 330 or may return to task 302 if additional pulses are to be generated. As an example, the control module 56 may adjust parameters of the pulses based on the feedback signal FB and perform another iteration of the method based on the adjusted parameters.

In order to stimulate nerve tissue using a traditional bipolar stimulation probe, as much as five times as much current may be needed for anodal stimulation, as opposed to cathodal stimulation. The current level or threshold for stimulating the nerve tissue may be determined by applying a current level and increasing the current level until a maximum nerve response is detected. The current level is no longer increased once a maximum nerve response is detected. As an example, a cathodal stimulation current may be 1 milli-ampere (mA) and an anodal stimulation may require up to 5 mA. In contrast, the current levels of the first and second pulses applied in the above-described method of FIG. 7 may be 1 mA each. As a result, a total of 2 mA of current may be supplied to the tissue for a single iteration of the method. Thus, the above-described method may reduce the amount of current used to stimulate the nerve tissue (e.g., 2 mA rather than 5 mA) and assures that the nerve tissue is cathodally stimulated, since both an anodal pulse and cathodal pulse are generated. The nerve tissue is stimulated regardless of the orientation of the electrodes 68. Also, the dually generated pulses can provide a more stable (or less erratic) response than applying a single anodal or cathodal pulse. This is because the first pulse may initially excite (or "prime") the nerve tissue, and the second pulse may stimulate the nerve tissue. In addition, the above-described method can excite nerve tissue at lower nerve thresholds (lower current levels) regardless of the orientation of the electrodes 68 relative to the nerve tissue.

Although the above-described method is primarily described to include generation of dual pulses (e.g., a first pulse in a first direction and a second pulse in a second direction), the method may include generation of any number of pulses. The method may include generating a series of first consecutive pulses in a first direction (e.g., sent via a cathode and/or a first probe tip of a dual tipped probe) while operating in the first mode and a series of second consecutive pulses in a second direction (sent via an anode and/or a second probe tip of the dual tipped probe) while operating in the second mode. The second series of pulses may be generated prior to the first series of pulses. Predetermined wait periods may be provided between consecutive pulses. The wait periods may have the same length or may have different lengths. By providing multiple consecutive pulses in a first direction and then multiple consecutive pulses in a second direction, less current may be supplied per pulse than when providing only a single pulse in a first direction and a single pulse in a second direction. This improves facilitation of nerve or neuro summation. Certain neural and/or cortical structures are better stimulated with multiple consecutive pulses per direction rather than a single pulse per direction. Certain neural and/or cortical structures may not be stimulated and/or adequately stimulated if only a single pulse per direction is provided, such as mapping of cortical motor tracks. Thus, by providing multiple consecutive pulses per direction, these types of structures are adequately stimulated. In another embodiment, the method includes alternating between positive and negative pulses.

The above-described tasks are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

Figure 9:
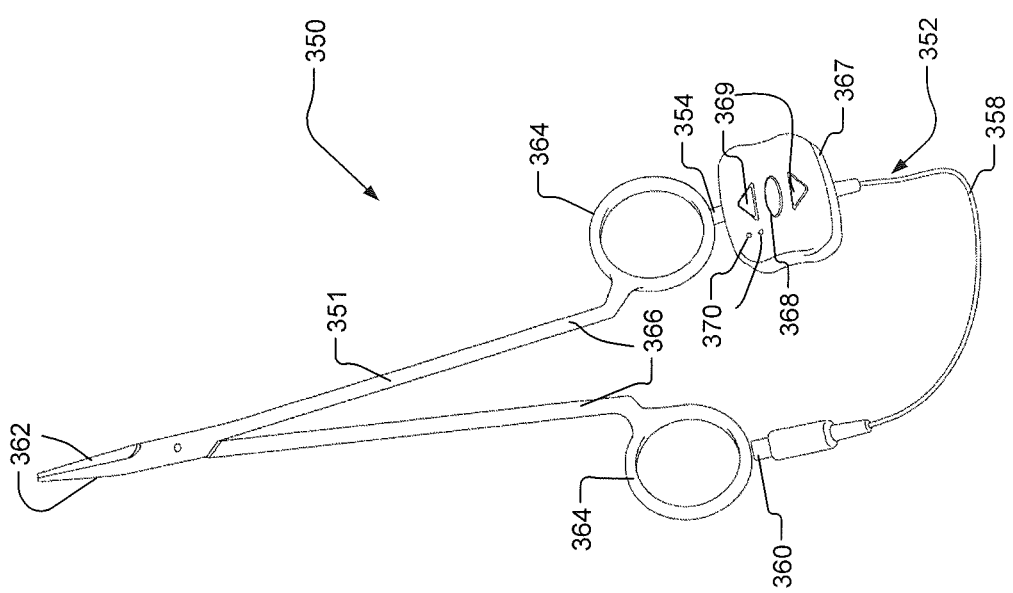
FIG. 9 is a perspective view of an instrument in accordance with the present disclosure.
Figure 11:
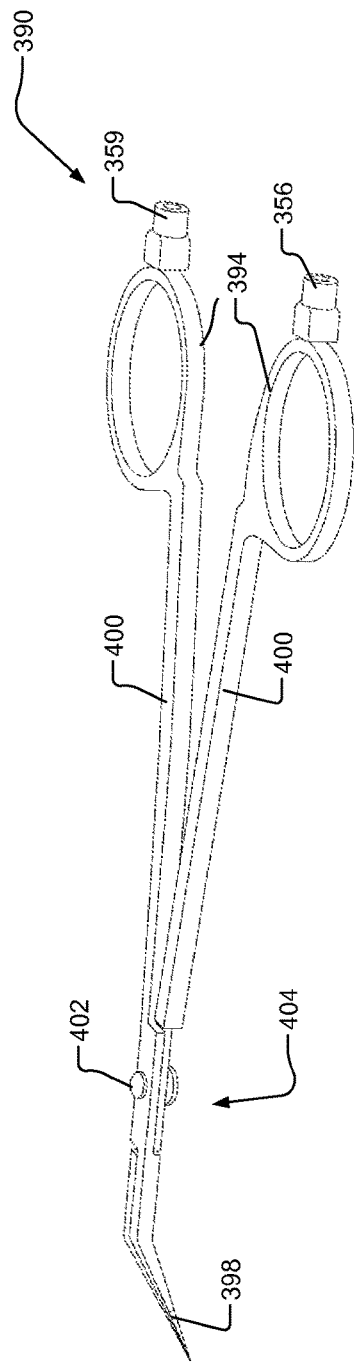
FIG. 11 is a perspective view of a tool configured to connect to a modular stimulation module in accordance with the present disclosure.
Figure 12:
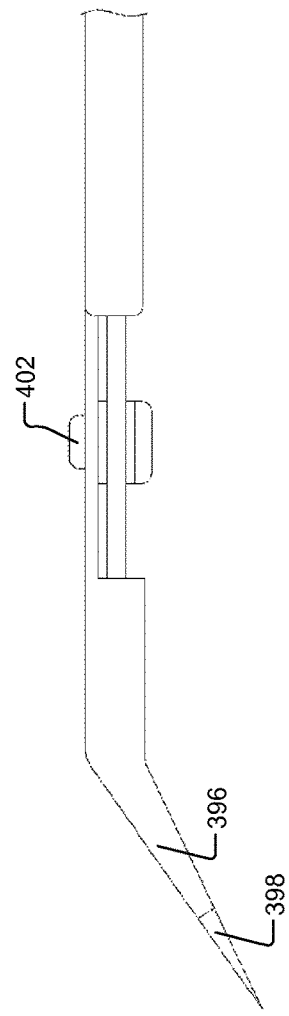
FIG. 12 is a side view of a portion of the tool of FIG. 11.
Figure 13:
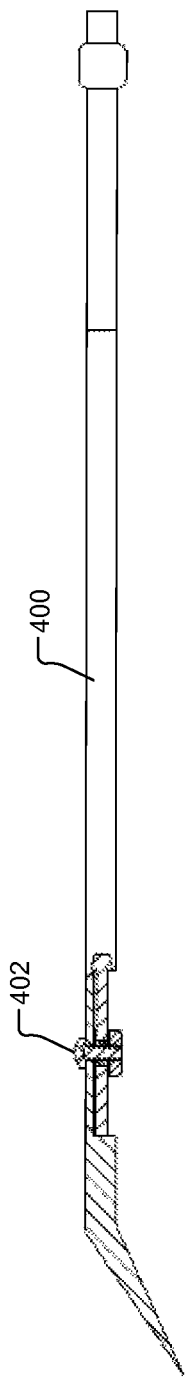
FIG. 13 is a perspective sectional view of a portion of the tool of FIG. 11.
Figure 14:
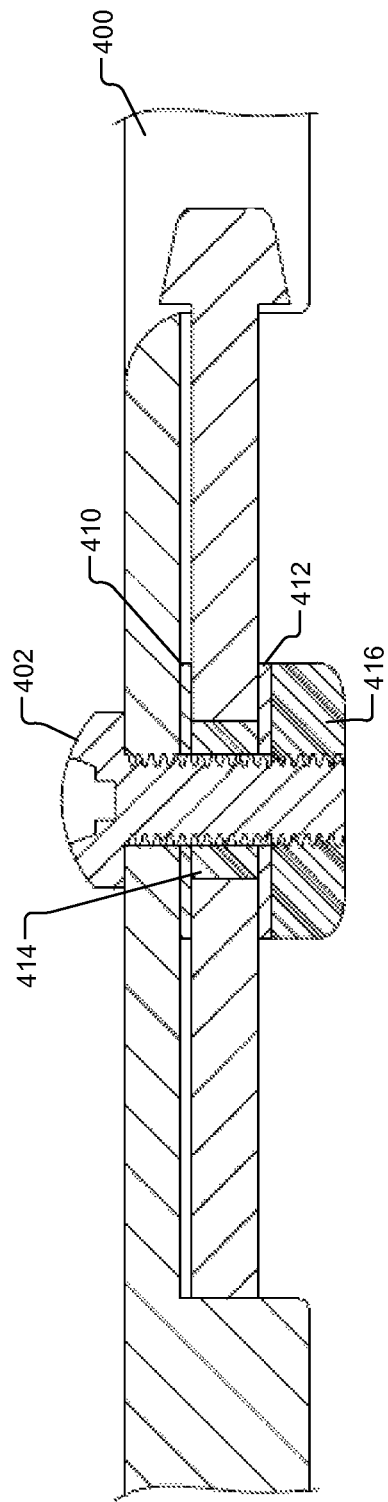
FIG. 14 is a perspective sectional view of a hinge portion of the tool of FIG. 11.
Figure 15:
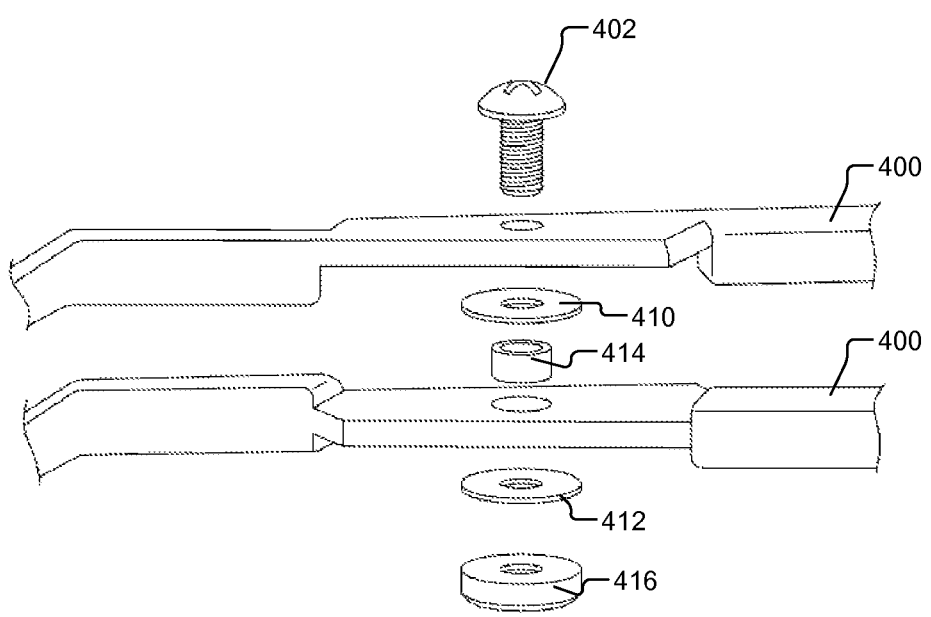
FIG. 15 is a perspective assembly view of the hinge portion of the tool of FIG. 11.
Figure 16A:
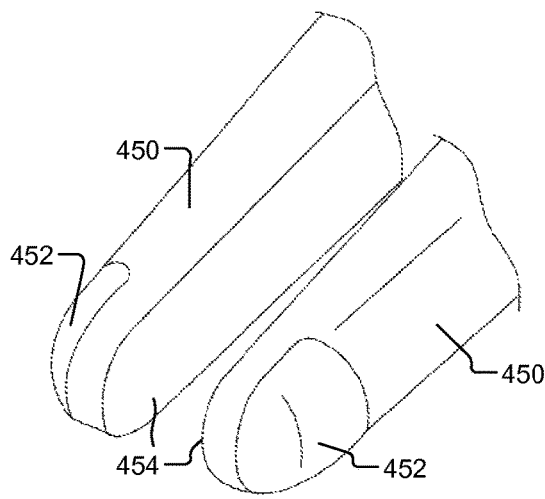
FIGS. 16A-D are perspective tip views of a tool having exposed tip patches in accordance with the present disclosure.
Figure 16B:
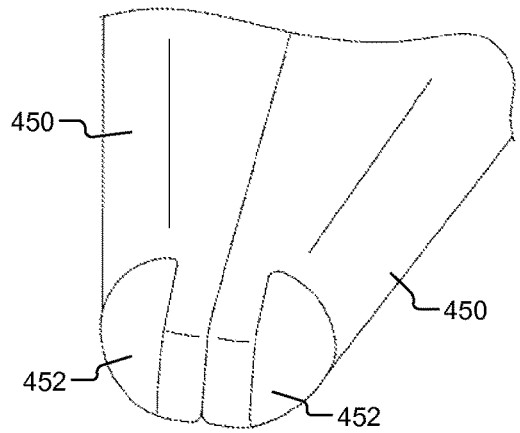
Figure 16C:
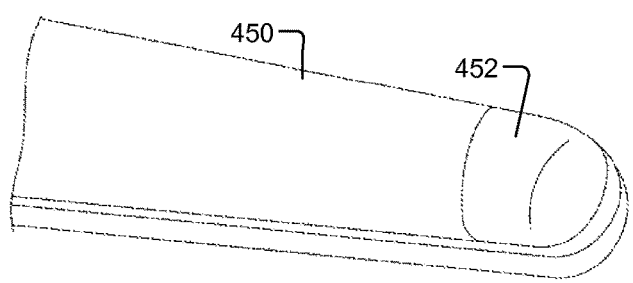
Figure 16D:
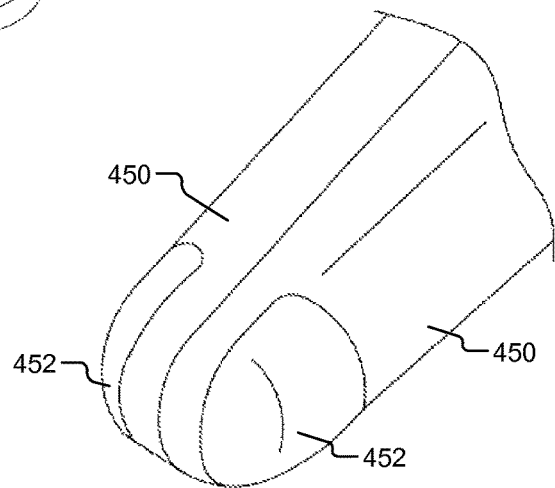
Figure 17A:
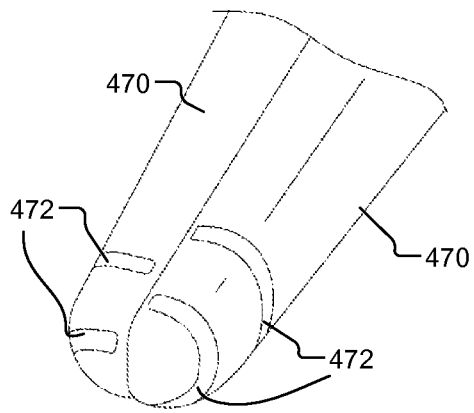
FIGS. 17A-D are perspective tip views of a tool having exposed helical traces in accordance with the present disclosure.
Figure 17B:
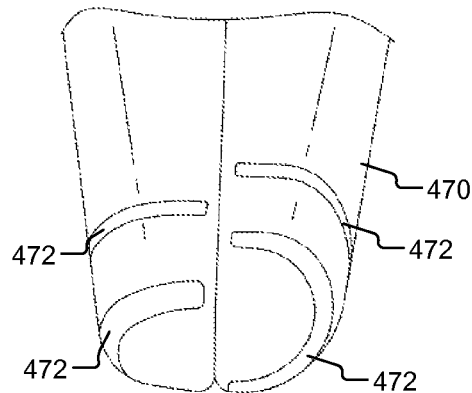
Figure 17C:
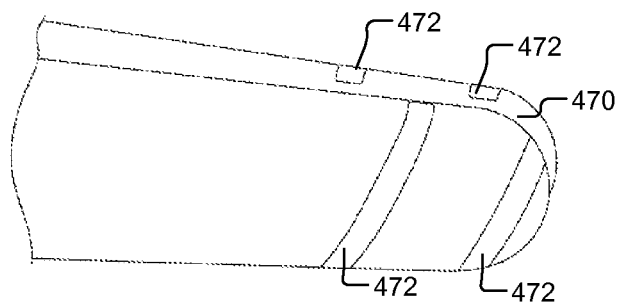
Figure 17D:
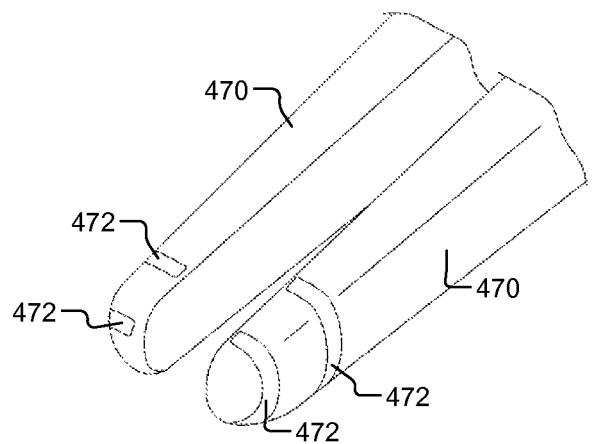
Figure 18A:
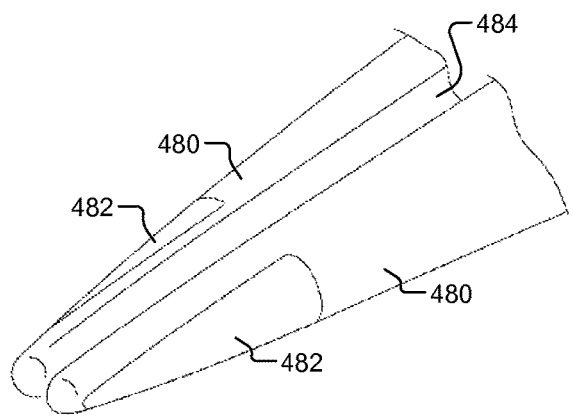
FIGS. 18A-D are perspective tip views of a tool having needle nose patches in accordance with the present disclosure.
Figure 18B:
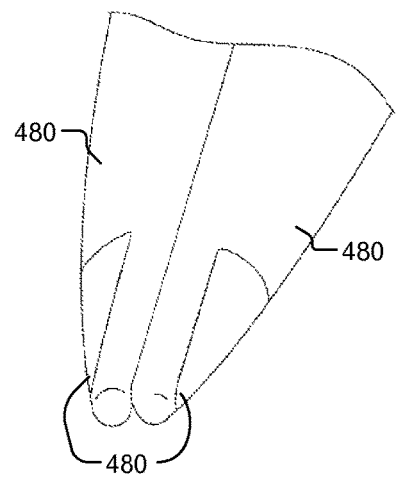
Figure 18C:
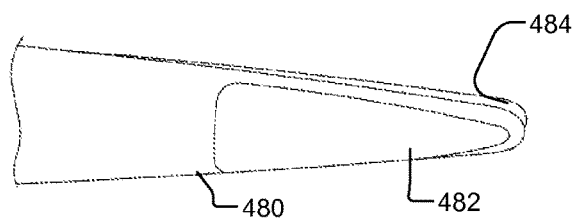
Figure 18D:
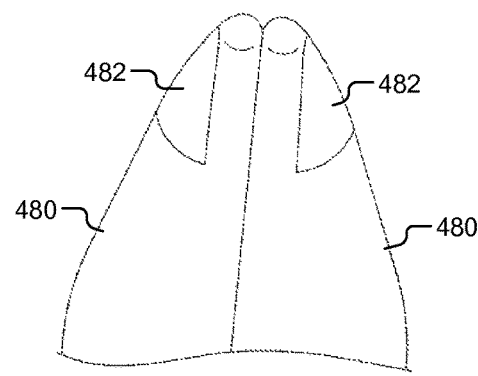
Figure 19A:
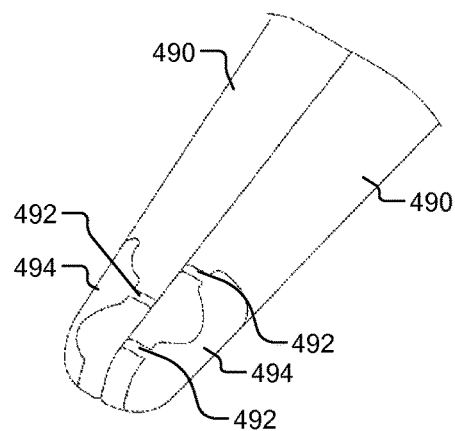
FIGS. 19A-E are perspective tip views of a tool having inner exposed and offset traces an exterior exposed patches in accordance with the present disclosure.
Figure 19B:
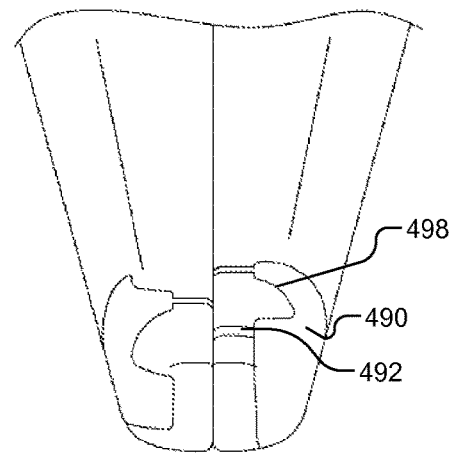
Figure 19C:
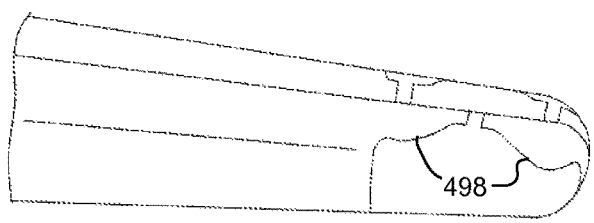
Figure 19D:
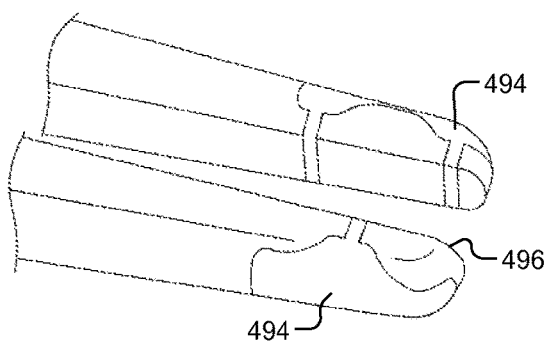
Figure 19E:
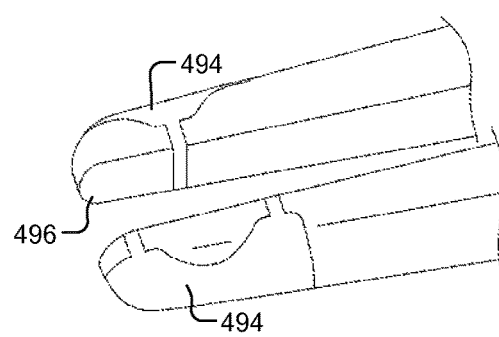

FIG. 9 shows an instrument 350 including a tool 351 and a modular stimulation module 352. The tool 351 may replace the tool 208 of FIG. 5. The instrument 350 has dual purposes. The instrument 350 functions as a tool and operates as a side-by-side bipolar stimulation probe. The modular stimulation module 352 shows an example of the modular stimulation module 202 of FIG. 5. Although the tool 351 is shown as being forceps, another tool may be used. The tool 351 may be designed to be reusable and sterilized between each use. The modular stimulation module 352 may be designed to be disposed after a single use. The modular stimulation module 352 includes (i) a first connector 354 that connects to a first connector 356 on the instrument 350, and (ii) a wire 358 that connects to a second connector 359 on the tool 351 via a second connector 360. The connectors 354, 360 are an example of the connectors 210 of FIG. 5. Examples of the connectors 356, 359 of the tool 351 are shown on a different tool in FIG. 11.

The tool 351 has a conductive inner core, which is coated in an insulative material. Tips 362 of the tool 351 have exposed conductive portions. Examples of the exposed conductive portions are shown in FIGS. 11, 12, and 16A-19E. The insulative material may include, for example, plastic, ceramic, or other suitable material. In one embodiment, the insulative material is a diamond like carbon (DLC) coating that is abrasion resistant. The insulative material isolates working portions (e.g., tips 362 and arms 366) of the tool 351. The tool 351 is shown as forceps having ring-shaped finger holding members 364, scissor style arms 366, and the tips 362.

The modular stimulation module 352 has a housing 367, a multi-function button 368, current adjustment buttons 369, and light emitting diodes (LEDs) 370. The multi-function button may be used as a capture button 368 for capturing events and screenshots. The multi-function button 368 may be pushed to capture an event and a screen shot may be provided on a display corresponding to the captured event. In one embodiment, the multi-function button 368 may be provided to turn ON and shut OFF the modular stimulation module 352. In one embodiment, when any of the buttons 364, 368 are pushed the modular stimulation module 352 is activated. Different pushing down and/or holding down patterns of the multi-function button 368 may be used to provide the different possible functions of the multi-function button 368. In one embodiment, power may be activated automatically (i.e. without pushing any of the buttons 364, 368) when: the modular stimulation module 352 is removed from packaging; the tool 351 is plugged into the modular stimulation module 352; the modular stimulation module 352 is plugged into the tool 351; and/or the modular stimulation module 352 is connected to the tool 351. The current adjustment buttons 369 may be used to increase or decrease the current of the pulses supplied to the tool 351. The LEDs 370 may indicate: whether the modular stimulation module 352 is ON; the modular stimulation module 352 is supplying current to the tool 351; status or activity of the wireless stimulation module 352; and/or whether the tips 362 of the tool 351 are in contact with tissue.

Figure 10:
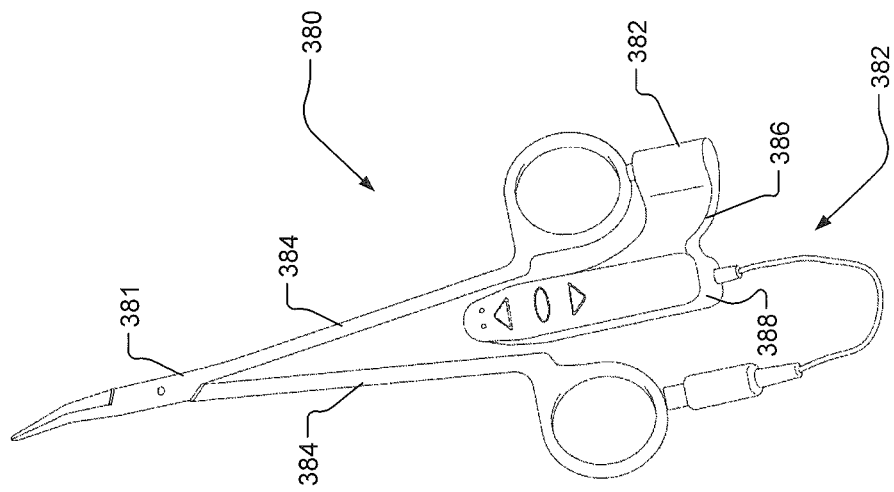
FIG. 10 is a perspective view of another instrument in accordance with the present disclosure.

FIG. 10 shows another example instrument 380 including a tool 381 and another example modular stimulation module 382. The instrument 380 has dual purposes. The instrument 380 functions as a tool and operates as a side-by-side bipolar stimulation probe. The tool 381 is show as forceps, but may be another type of instrument. The modular stimulation module 382 is similar to the modular stimulation module 352 of FIG. 9, but is shaped to partially be disposed between scissor shaped arms 384 of the tool 381. The modular stimulation module 382 is also shaped to minimize interference between fingers of a surgeon when using the instrument 380. The modular stimulation module 382 includes (i) a first portion 386 that connects to the tool 381, and (ii) a second portion 388 that extends between the scissor-shaped arms 384. A majority of the hardware contained within the modular stimulation module 382 may be located in the second portion 388.

FIGS. 11-15 show another example tool 390 that is configured to connect to a modular stimulation module (e.g., one of the modular stimulation modules 202, 352, 382 of FIGS. 5, and 9-10). The tool 390 is shown as forceps having the connectors 356, 359 on ring-shaped finger holding members 394. The tool 390 has tips 396 with conductive elements 398 exposed on sides of the tips 396. Although each of the conductive elements 398 are shown as single (one-piece) items, each of the conductive elements 398 may include multiple conductive elements connected in series. The exposed portions of the conductive elements function as contacting elements for contacting, for example, tissue. As an alternative, the conductive elements 398 may be connected to contacting elements having a same contacting surface area as the shown exposed portions of the conductive elements 398. The tool 390 includes scissor type arms 400 that are connected via a fastener 402 in a hinge area 404. The scissor type arms 400 include the conductive elements 398. The fastener 402 extends through holes in the arms 400. The fastener 402 may extend through the holes in the arms 400, washers 410, 412, an insert 414, and be screwed into a nut 416. The insert 414 may be disposed within the hole of one of the arms 400. The washer 410 may be disposed between the arms 400. The washer 412 may be disposed between the nut 416 and one of the arms 400 (e.g., the arm having the hole for the insert 414). The washers 410, 412 and the insert 414 may be referred to as insulative bushings. In one embodiment, the fastener 402 is conductive (e.g., made of one or more conductive and/or metallic materials) and is isolated from the arms 402 due to the insulative coating on the arms 402 and the insulative bushings 410, 412, 414. In another embodiment, the fastener 402 is formed of one or more insulative materials (e.g., ceramic or a polymer material).

The above-described tools may have various different style tips with different exposed surfaces (or conductive elements). The exposed surfaces may refer to: portions of the tips and/or tools that are not coated with an insulative material; and/or may refer to exposed conductive portions of the tools that are electrically connected to a modular stimulation module via connectors, where the connectors are located elsewhere on the tools. The following FIGS. 16A-19E disclose some examples of different style tips that may be used.

FIGS. 16A-D show tips 450 of a tool having exposed tip patches 452. The tip patches 452 do not face each other and are on opposite exterior sides of the tips 450. Each of the tip patches 452 extend around an exterior portion of a corresponding one of the tips 450. When the tips 450 are in a closed state (i.e. the tips 450 are touching each other), the tip patches 452 do not contact each other and there is a predetermined distance between the tip patches 452. The predetermined distance is designed to prevent shorting or shunting of current between the tip patches 452. As an example, the tip patches 452 may be 1-2 milli-meter (mm) apart from each other when the tips 450 are in the closed state. The tip patches 452 are not on inner sides 454 of the tips 450.

FIGS. 17A-D show tips 470 of a tool having exposed helical traces 472. The helical traces 472 extend around exterior sides of the tips 470. The ones of the helical traces 472 on a first one of the tips 470 are offset from the ones of the helical traces 472 on a second one of the tips 470. As an example, the helical traces on a first tip are more distally located than helical traces on the second tip. The helical traces 472 are in an alternating relationship, such that: a first trace on a first tip is more distally located than a first trace on the second tip; the first trace on the second tip is more distally located than a second trace on the first tip; and the second trace on the first tip is more distally located than a second trace on the second tip.

FIGS. 18A-D show tips 480 of a tool having needle nose patches 482. The tip patches 482 do not face each other and are on opposite exterior side of the tips 480. Each of the tip patches 482 extend around an exterior portion of a corresponding one of the tips 480. When the tips 480 are in a closed state (i.e. the tips 480 are touching each other), the tip patches 482 do not contact each other and there is a predetermined distance between the tip patches 482. The predetermined distance is designed to prevent shorting or shunting of current between the tip patches 482. The tip patches 482 are not on inner sides 484 of the tips 480.

FIGS. 19A-E show tips 490 of a tool having inner exposed and offset traces 492 in addition to exterior exposed patches 494. The exterior exposed patches 494 do not face each other and are on opposite side of the tips 490. Each of the tip patches 494 extend around an exterior portion of a corresponding one of the tips 490. The traces 492 extend from the patches 494 and around inner sides 496 of the tips 490. When the tips 490 are in a closed state (i.e. the tips 490 are touching each other), the traces 492 do not contact each other and the tip patches 494 do not contact each other. When the tips 490 are closed, the traces 492 and the tip patches 494 are predetermined distances from teach other. The predetermined distances are designed to prevent shorting or shunting of current between the traces 492, between the tip patches 494, and/or between the traces 492 and the tip patches 494. The tip patches 494 are also shaped to maintain a minimum predetermined distance (i) between each of the trace(s) that are on a first tip and the tip patch on the second tip, and (ii) between each of the traces(s) that are on the second tip and the tip patch on the first tip. For example, the tip patches 494 have notches 498 that are in alignment with the opposing and corresponding ones of the traces 492. The tip patches 494 are not on inner sides 496 of the tips 480.

Sizes of the exposed traces and patches of the above-described tools are minimized to limit the amount of tissue exposed to current. The sizes of traces and patches may also be minimized to focus current being applied to certain target tissue areas. The tips of exposed surfaces (e.g., traces or patches) of each of the tools are shaped such that during use a first tip is able to contact nerve tissue and the other tip is able to contact other tissue of the same nerve tissue or other anatomical element (tissue, muscle, skin, blood, etc.) of the same patient.

Each of the above-described patches 452, 482, 492 and traces 472 of FIGS. 16A-19E allow for current to be directed away from the corresponding tip in up to 180° relative to a longitudinal axis of the tip. This is because of the patches 452, 482, 492 and traces 472 extending around the exterior portions of the corresponding tips. As a result, the patches 452, 482, 492 and traces 472 provide 360° of possible current emission. Also, since the tools of the tips may be connected to a modular stimulation module (e.g., one of the modular stimulation modules 202, 352, 382) and pulses may be transmitted from each of the tips, the tips provide omni-directional tools/instruments. The traces 492 and patches 494 of the tips 490 of FIGS. 19A-E provide 360° of possible current emission by each of the tips 490.

Another contemporary solution to solving the traditional electrode orientation problem includes generating biphasic stimulation waveforms. This includes generating a first pulse in a first (e.g., anodal) direction and a second pulse in a second (e.g., cathodal) direction via respective power sources. The first pulse may be, for example, a +5 volts (V) pulse and the second pulse may be a −5 V pulse. The generation of biphasic waveforms requires a dual power supply circuit and/or dual power sources, which requires more complex circuits and consumption of more power than a circuit generating dual monophasic waveforms (e.g., the waveforms generated using the modular stimulation module 202 of FIG. 5 and the method of FIG. 7). Monophasic waveforms refer to waveforms having pulses that are positive or negative pulses, but are not both positive and negative pulses. In other words, both pulses have the same polarity. The dual monophasic waveform implementations are less complex, consume less power and require less space than the biphasic waveform implementations. Thus, the dual monophasic waveform implementations are more feasible for small handheld battery-powered stimulators.

The above-disclosed examples eliminate a need for an anodal needle and wire to terminate an anodal (or referential ground) electrode. The above-disclosed examples eliminate concern of probe orientation relative to nerve anatomy and achieve lower nerve thresholds required to evoke a nerve action potential.

The wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium include nonvolatile memory circuits (such as a flash memory circuit or a mask read-only memory circuit), volatile memory circuits (such as a static random access memory circuit and a dynamic random access memory circuit), and secondary storage, such as magnetic storage (such as magnetic tape or hard disk drive) and optical storage.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

None of the elements recited in the claims is intended to be a means-plus-function element within the meaning of 35 U.S.C. § 112(f) unless an element is expressly recited using the phrase "means for", or in the case of a method claim using the phrases "operation for" or "step for".

What is claimed is:

1. A wireless handheld bipolar stimulation probe comprising:
    a housing portion having a grip configured to be held by a user during use of the wireless handheld bipolar stimulation probe;
    an elongated member extending from the housing portion to a first electrode and a second electrode, wherein the first electrode is spaced apart from the second electrode on the elongated member;
    housed in the housing portion;
        (1) a control module configured to stimulate a nerve tissue of a patient based on recalled parameters by generating (i) a first output signal indicative of a first pulse to be output from the first electrode, and (ii) a second output signal indicative of a second pulse to be output from the second electrode, wherein both of the first pulse and the second pulse is monophasic such that the first pulse and second pulse are selected one of either positive or negative;
        (2) a first switch electrically connected to the first electrode and the control module; and
        (3) a second switch electrically connected to the second electrode and the control module; and
        (4) a physical layer module configured to wirelessly communicate with a nerve integrity monitoring device;
    wherein the control module generates a switch control signal to the first and second switches to send from the bipolar stimulation probe (i) the first pulse on the first electrode based on the first output signal and (ii) the second pulse on the second electrode based on the second output signal;
    wherein the first electrode and the second electrode alternate between operation as a cathode and an anode by operation of the first switch or the second switch to each operate as both the cathode and the anode such that both of the provided first pulse and second pulse are monophasic when the first pulse and the second pulse are sent from the first electrode and the second electrode;
    wherein the first electrode and the second electrode are configured to be positioned adjacent the nerve tissue by the user holding and positioning the wireless handheld bipolar stimulation probe during use such that the first pulse is generated based on the first output signal and the second pulse is generated based on the second output signal and the switch control signal changes states of at least one of the first switch or the second switch in the bipolar stimulation module such that the first pulse and the second pulse are provided in opposite directions along the nerve tissue;
    wherein the nerve integrity monitoring device is configured to analyze the first pulse and the second pulse provided in opposite directions along the nerve tissue in the patient.

2. The bipolar stimulation probe of claim 1, wherein:
    the control module is configured to generate the switch control signal to further (i) change an operating mode of the bipolar stimulation probe, and (ii) control states of the first and second switches;
    during a first mode, (i) the first switch is in a first state and delivers the first pulse to the first electrode through the first switch, and (ii) the second switch is in a first state and receives return current from the patient as a result of the first pulse through the second switch; and during a second mode, (i) the second switch is in a second state and delivers the second pulse to the second electrode through the second switch, and (ii) the first switch is in a second state and receives return current from the patient as a result of the second pulse through the first switch;

wherein both the first pulse and the second pulse are supplied from a single power source.

3. The bipolar stimulation probe of claim 2, wherein the control module is configured to wait a predetermined period between generating the first output signal and the second output signal to account for a refractory period of time of the nerve tissue.

4. The bipolar stimulation probe of claim 2, wherein:
the control module is configured to stimulate the nerve tissue of the patient by generating (i) a first plurality of output signals indicative of a first plurality of pulses to be sent from the first electrode, and (ii) a second plurality of output signals indicative of a second plurality of pulses to be sent from the second electrode, wherein the first plurality of pulses and the second plurality of pulses are monophasic, wherein the first plurality of pulses includes the first pulse, and the second plurality of pulses includes the second pulse; and the first and second switches are configured to send from the bipolar stimulation probe (i) the first plurality of pulses on the first electrode based on the first plurality of output signals, and then (ii) the second plurality of pulses on the second electrode based on the second plurality of output signals;

wherein the elongated member has a "Y"-shape extending from the first electrode and the second electrode;

wherein the first plurality of pulses and the second plurality of pulses are provided in opposite directions along the nerve tissue.

5. The bipolar stimulation probe of claim 1, further comprising an amplification module configured to:
receive a first input based on the first output signal;
amplify the first input to generate the first pulse;
receive a second input based on the second output signal; and
amplify the second input to generate the second pulse.

6. The bipolar stimulation probe of claim 1, further comprising a filter configured to:
receive a first input based on the first output signal;
filter the first input to generate a first filtered output;
receive a second input based on the second output signal; and
filter the second input to generate a second filtered output,
wherein the first and second switches are configured to provide (i) the first pulse based on the first filtered output to the first electrode, and (ii) the second pulse based on the second filtered output to the second electrode.

7. The bipolar stimulation probe of claim 1, further comprising a digital-to-analog converter configured to convert (i) the first output signal to a first analog signal, and (ii) the second output signal to a second analog signal,
wherein the first and second switches are configured to provide (i) the first pulse based on the first analog signal to the first electrode, and (ii) the second pulse based on the second analog signal to the second electrode.

8. The bipolar stimulation probe of claim 1, further comprising a feedback module configured to (i) detect a first voltage across the first electrode and the second electrode during generation of the first pulse, (ii) detect a second voltage across the first electrode and the second electrode during generation of the second pulse, and (iii) generate a feedback signal based on the first voltage or the second voltage,
wherein the control module is configured to generate a third pulse based on the first voltage or the second voltage.

9. The bipolar stimulation probe of claim 8, wherein:
the feedback module comprises a transconductance amplifier;
the transconductance amplifier is configured to (i) convert the first voltage to a first current, and (ii) the second voltage to a second current; and
the control module is configured to generate the third pulse based on the first current or the second current.

10. A system comprising:
the bipolar stimulation probe of claim 1;
a sensor configured to detect signal activity in the area of the patient due to at least one of the first pulse and the second pulse; and
the nerve integrity monitoring device configured to (i) based on the first pulse and the second pulse, monitor the signal activity in the area of the patient, (ii) determine when the first pulse and the second pulse are generated, and (iii) based on when the first pulse and the second pulse are generated, filter out portions of the signal activity.

11. The system of claim 10, wherein:
the signal activity includes the first pulse, the second pulse and at least one artifact of the first pulse and the second pulse; and
the nerve integrity monitoring device is configured to filter out the at least one artifact during a rejection period and monitor electromyography signals during a first monitoring period,
the first monitoring period is subsequent to the rejection period.

12. The system of claim 11, wherein the nerve integrity monitoring device is configured to:
filter out a first artifact of the at least one artifact of the first pulse or a second artifact of the at least one artifact of the second pulse during the rejection period; and
the first monitoring period is subsequent to the rejection period and corresponds to both the first pulse and the second pulse.

13. The system of claim 11, wherein the nerve integrity monitoring device is configured to:
filter out a first artifact of the at least one artifact of the first pulse during the first rejection period;
filter out a second artifact of the at least one artifact of the second pulse during a second rejection period;
monitor a first electromyography signal during the first monitoring period;
monitor a second electromyography signal during a second monitoring period;
the first monitoring period is based on the first pulse; and
the second monitoring period is based on the second pulse.

14. A system comprising:
the bipolar stimulation probe of claim 1; and
the nerve integrity monitoring device configured to generate a first request signal,
wherein the control module is configured to, based on the first request signal, generate the first output signal or the second output signal.

15. The system of claim 14, wherein:
the bipolar stimulation probe comprises a feedback module configured to (i) monitor a voltage across the first electrode and the second electrode, and (ii) generate a feedback signal based on the voltage;

the control module is configured to (i) determine a parameter of the feedback signal, and (ii) wirelessly transmit the parameter via the physical layer module to the nerve integrity monitoring device;

the nerve integrity monitoring device is configured to (i) generate a second request signal based on the parameter, and (ii) wirelessly transmit the second request signal back to the physical layer module; and the control module is configured to generate a third pulse based on the second request signal.

16. A wireless handheld bipolar stimulation probe comprising:

a housing portion having a grip configured to be held by a user during use of the wireless handheld bipolar stimulation probe;

a first electrode separated from a second electrode and both separated from the housing portion;

housed in the housing portion;
  (1) a control module configured in a selected mode to generate (i) a first stimulation pulse having a selected polarity that is one of positive or negative to be output from the first electrode, and (ii) a second stimulation pulse having the selected polarity to be output from the second electrode, wherein each of the first stimulation pulse and the second stimulation pulse is monophasic such that each of the first stimulation pulse and the second stimulation pulse has the same selected polarity;
  (2) a first switch electrically connected to the first electrode from the control module;
  (3) a second switch electrically connected to the second electrode from the control module; and
  (4) a single power source configured to be connected to both the first electrode and the second electrode;

at least one of a console interface module or a nerve integrity monitoring system;

wherein the control module is configured to wirelessly communicate with the at least one of the console interface module or the nerve integrity monitoring system to (i) control stimulation of a nerve tissue of a patient by the generation of the first stimulation pulse and the second stimulation pulse and (ii) operate the first switch or second switch;

wherein the first and second switches are configured to switch to output from the bipolar stimulation probe (i) the first stimulation pulse on the first electrode based on a first output signal, and (ii) the second stimulation pulse on the second electrode based on a second output signal;

wherein the first electrode and the second electrode alternate, due to operation of the first switch or the second switch, to operate as both a cathode and an anode to provide each of the first stimulation pulse and second stimulation pulse to be monophasic and have the selected polarity when the first pulse and the second pulse are sent from the first electrode and the second electrode;

wherein the first stimulation pulse and the second stimulation pulse are configured to travel along the nerve tissue from the respective first electrode and second electrode based on the configuration of the first and second switches and the control of the control module;

wherein both the first stimulation pulse and the second stimulation pulse are generated from the single power source;

wherein the first electrode and the second electrode are configured to be positioned adjacent a nerve tissue by the user holding and positioning the wireless handheld bipolar stimulation probe during use such that the first stimulation pulse and the second stimulation pulse are provided to the nerve tissue.

17. The bipolar stimulation probe of claim 16, wherein the first stimulation pulse and the second stimulation pulse are provided in opposite directions along the nerve tissue.

* * * * *